United States Patent
Kanazawa et al.

(10) Patent No.: US 7,608,716 B2
(45) Date of Patent: Oct. 27, 2009

(54) PYRAZOLONAPHTHYRIDINE DERIVATIVE

(75) Inventors: Hashime Kanazawa, Hamura (JP);
Tomoji Aotsuka, Hamura (JP);
Kentarou Kumazawa, Hamura (JP);
Kouki Ishitani, Hamura (JP); Takashi Nose, Hamura (JP)

(73) Assignee: Aska Pharmaceutical Co., Ltd., Tokyo (JP)

( * ) Notice: Subject to any disclaimer, the term of this patent is extended or adjusted under 35 U.S.C. 154(b) by 78 days.

(21) Appl. No.: 10/533,806

(22) PCT Filed: Nov. 5, 2003

(86) PCT No.: PCT/JP03/14119

§ 371 (c)(1),
(2), (4) Date: May 5, 2005

(87) PCT Pub. No.: WO2004/041819

PCT Pub. Date: May 21, 2004

(65) Prior Publication Data

US 2006/0040972 A1    Feb. 23, 2006

(30) Foreign Application Priority Data

Nov. 6, 2002    (JP) .............................. 2002-322000

(51) Int. Cl.
*A61K 31/4375* (2006.01)
*C07D 471/14* (2006.01)
*C07D 471/16* (2006.01)

(52) U.S. Cl. ............................ 546/82; 514/293; 546/84

(58) Field of Classification Search .................... 546/84; 514/293

See application file for complete search history.

(56) References Cited

U.S. PATENT DOCUMENTS

| 5,281,610 A * | 1/1994 | Suzuki et al. ............... 514/293 |
| 6,117,875 A | 9/2000 | Shimazaki et al. |
| 6,352,989 B1 | 3/2002 | Miyazaki et al. |

FOREIGN PATENT DOCUMENTS

| CA | 2 388 658 | 11/2000 |
| EP | 0526840 | * 7/1991 |
| EP | 526840 | 2/1993 |
| EP | 1 145 714 | 10/2001 |
| EP | 1 236 725 | 9/2002 |
| JP | 6-100561 | 4/1994 |
| JP | 7-10875 | 1/1995 |
| WO | 97/24355 | 7/1997 |
| WO | 99/06404 | 2/1999 |
| WO | 99/37622 | 7/1999 |
| WO | 00/26218 | 5/2000 |
| WO | 00/32192 | 6/2000 |
| WO | 00/66584 | 11/2000 |
| WO | 01/42244 | 6/2001 |

* cited by examiner

*Primary Examiner*—Rita J Desai
(74) *Attorney, Agent, or Firm*—Wenderoth, Lind & Ponack, LLP.

(57) ABSTRACT

The target is to provide PDE IV inhibitors which have a highly potent anti-asthmatic and/or COPD-prophylactic/therapeutic profile with unexpectedly excellent safety. A compound of the formula (1):

wherein A is phenyl, pyridyl, 1-oxypyridyl, or thienyl, which may be unsubstituted or optionally substituted with one or more members selected from the group consisting of hydroxyl, halogen, cyano, nitro, lower alkyl, lower alkoxy, lower alkylcarbonyloxy, amino, carboxyl, lower alkoxycarbonyl, carboxy-lower alkylene, lower alkoxycarbonyl-lower alkylene, lower alkylsulfonyl, lower alkylsulfonylamino, and ureido; $R^1$ is a group selected from the group consisting of hydrogen, hydroxyl, halogen, cyano, nitro, lower alkoxy, amino, carboxyl, and lower alkoxycarbonyl; $R^2$ is hydrogen or lower alkyl; and m is an integer of 1 to 3; or a pharmaceutically acceptable salt thereof, possesses highly excellent PDE IV-specific inhibitory actions and is useful as an anti-asthmatic drug and/or a prophylactic/therapeutic drug for COPD with high safety.

2 Claims, No Drawings

PYRAZOLONAPHTHYRIDINE DERIVATIVE

This application is a U.S. national stage of International Application No. PCT/JP2003/014119 filed Nov. 5, 2003.

FIELD OF THE INVENTION

The present invention relates to novel condensed naphthyridine derivatives that inhibit phosphodiesterase (hereinafter, referred to as "PDE") IV, or pharmaceutically acceptable salts thereof, and to pharmaceutical compositions comprising the same.

BACKGROUND OF THE INVENTION

PDEs are enzymes which hydrolyze intracellular cyclic AMP (cAMP) and intracellular cyclic GMP (cGMP) and widely distributed in vivo in various tissues and organs. Up to now, it has been known that PDEs are classified into 7 isoenzyme families, i.e., type I to VII PDEs (PDE I to VII), according to their properties. Among them, PDE IV is known to be an enzyme which is predominantly present in airway smooth muscle cells and a wide variety of inflammatory cells, i.e., neutrophils, eosinophils, lymphocytes, etc. and selectively breaks down cAMP.

In addition, it has been known that an elevation of cAMP levels in airway smooth muscle cells leads to relaxation of the airway smooth muscles. An increase of cAMP levels in inflammatory cells has also been known to suppress an activation of inflammatory cells, including, for example, a release of cytotoxic proteins from eosinophils, etc.

Therefore, if PDE IV predominantly located in airway smooth muscle cells and inflammatory cells is inhibited by inhibitors selective for said isozyme form, an elevation of cAMP levels would be induced in such cells. As a result, it would be expected to elicit bronchodilator actions via relaxing airway smooth muscles and anti-inflammatory actions through suppressing inflammatory cell activation. As seen, for example, in Barnette, PROGRESS IN DRUG RESEARCH, USA, Vol. 53, pp. 193-229 (1999) (non-patent document No. 1), such selective inhibitors of PDE IV would be expected to become excellent anti-asthmatic agents and therapeutic agents for chronic obstructive pulmonary disease (COPD).

Up to now, it has been known that theophylline which is a xanthine derivative, rolipram, which is a catechol derivative, etc., are inhibitors of PDE IV. Theophylline inhibits PDE in various tissues due to its non-selectivity for individual isozymes, thereby exerting not only a bronchodilator activity to be targeted but also extra actions on heart, CNS, etc. Although rolipram is observed to be selective for PDE IV, it is easily transferred into the CNS due to its property of being absorbed. Therefore, rolipram has a drawback that it induces adverse central side-effects such as an emetic action.

Over the past decade, many pharmaceutical companies have focused on the inhibition of PDE IV for the treatment of asthma. The biological studies on the PDE IV isozyme and the structure-activity relationship of said inhibitors have recently been reviewed in the literature. In such processes, it has been pointed out that in general the therapeutic utility of selective PDE IV inhibitors, such as the prototypical agent rolipram, have been hampered by nausea and emesis limiting their therapeutic potential (J. Med. Chem., 41: 2268 to 2277 (1998): non-patent document No. 2).

It recently becomes known that PDE IV inhibitors produce inhibition of drug-metabolizing enzymes such as CYP2D6 and CYP3A4, thereby raising a variety of adverse side-actions. Therefore, there is still a desire to develop a PDE IV inhibitor free of affecting the drug-metabolizing enzymes.

Under these circumstances, in order to find out pharmaceutical drugs having an excellent anti-asthmatic efficacy and/or a prophylactic or therapeutic efficacy on COPD via minimizing undesirable side-effects in tissues and organs other than bronchial smooth muscles and inflammatory cells, various PDE IV inhibitors have been screened and examined.

For instance, with an aim at such inhibitors with improved selectivity for PDE IV, various compounds have been proposed including naphthalene derivatives (e.g., Patent document No. 1: JP, A, 10-226647 (1998)), catechol diethers derivatives (e.g., Patent document No. 2: JP, A, 2001-527508), 2,3-di-substituted pyridine derivatives (e.g., Patent document No. 3: JP, A, 2001-354655), etc. Further, for the purpose of developing not only anti-asthmatic agents but also pharmaceutical agents for preventing and treating a wide range for diseases, PDE IV-inhibitory compounds having a naphthyridine ring have been proposed (for example, Patent document No. 4: JP, A, 7-10875 (1995); Patent document No. 5: WO, A, 96/06843; Patent document No. 6: JP, A, 11-106385 (1999); Patent document No. 7: JP, A, 2002-138089; Patent document No. 8: WO, A, 99/02527; Patent document No. 9; WO, A, 99/38867; Patent document No. 10; WO, A, 01/42244; etc.).

Whereas, in connection with compounds where a heterocyclic ring is condensed to a naphthyridine ring are disclosed compounds having anti-inflammatory, immunoregulatory, analgesic, and antipyretic actions (for example, Patent document No. 11: JP, A, 5-132484 (1993), Patent document No. 12: JP, A, 6-100561 (1994)) and compounds having anti-inflammatory, immunoregulatory, bronchodilator, and hair-growing actions (for example, Patent document No. 13: JP, A, 5-194515 (1993), Patent document No. 14: JP, B2, 3016905); however, no inhibitory action on PDE IV is indicated in these prior art compounds.

[Patent document No. 1] JP, A, 10-226647 (1998)
[Patent document No. 2] JP, A, 2001-527508
[Patent document No. 3] JP, A, 2001-354655
[Patent document No. 4] JP, A, 7-10875 (1995)
[Patent document No. 5] WO, A, 96/06843
[Patent document No. 6] JP, A, 11-106385 (1999)
[Patent document No. 7] JP, A, 2002-138089
[Patent document No. 8] WO, A, 99/02527
[Patent document No. 9] WO, A, 99/38867
[Patent document No. 10] WO, A, 01/42244
[Patent document No. 11] JP, A, 5-132484 (1993)
[Patent document No. 12] JP, A, 6-100561 (1994)
[Patent document No. 13] JP, A, 5-194515 (1993)
[Patent document No. 14] JP, B2, 3016905
[Non-patent document No. 1] PROGRESS IN DRUG RESEARCH, (USA), 53, pp. 193-229 (1999)
[Non-patent document No. 2] JOURNAL OF MEDICINAL CHEMISTRY, (USA), 41, pp. 2268-2277 (1999)

SUMMARY OF THE INVENTION

The aforementioned compound groups are still unsatisfactory in view of solving the problems, i.e., of minimizing unfavorable side effects in other tissues/organs than airway smooth muscle cells and inflammatory cells, in order to develop and provide drugs with excellent anti-asthmatic and/or COPD-preventing/treating profiles.

There is a great desire to find an advantageously safe drug having not only a highly specific-inhibitory action on PDE IV but also an excellent anti-asthmatic and/or COPD-preventing/treating action.

The present inventors have conducted an extensive research on various compounds in order to solve the above problems. As a result, the present inventors have succeeded in producing unique pyrazolo[4,3-c][1,8]naphthyridin-4 (5H)-one derivatives which are derived from the compound having a naphthyridine skeleton (disclosed in WO, A, 01/42244) by condensing a imidazole ring to a specific site of the naphthyridine ring thereof and finding that these novel pyrazolo[4,3-c][1,8]naphthyridin-4 (5H)-one derivatives are not only pharmacologically advantageous over the conventional PDE IV inhibitors, but also qualified as excellently safer drugs than the conventional PDE IV inhibitors because it is perceivable that there is a great difference between their pharmacologically-effective dose and their effective dose for inhibiting drug-metabolizing enzymes. Thus, the present inventors have succeeded in accomplishing this invention.

The present invention, as described herein below, encompasses 1-unsubstituted or optionally 1-substituted pyrazolo[4,3-c][1,8]naphthyridin-4 (5H)-one derivatives having an unsubstituted or optionally substituted phenyl, pyridyl, 1-oxypyridyl or thienyl group via 1 to 3 methylene chains on the 3 position of the pyrazolo[4,3-c][1,8]-naphthyridin-4 (5H)-one nucleus.

The present invention provides the following:
1) A compound of the formula (1):

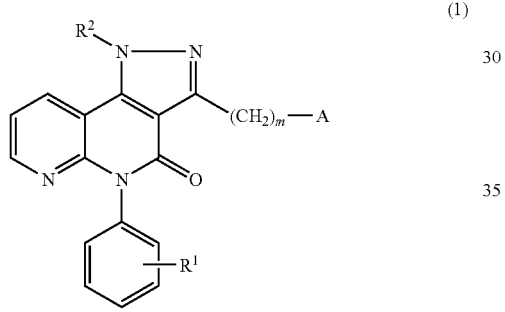

wherein:
A is phenyl, pyridyl, 1-oxypyridyl, or thienyl, which may be unsubstituted or optionally substituted with one or more members selected from the group consisting of hydroxyl, halogen, cyano, nitro, lower alkyl, lower alkoxy, lower alkylcarbonyloxy, amino, carboxyl, lower alkoxycarbonyl, carboxy-lower alkylene, lower alkoxycarbonyl-lower alkylene, lower alkylsulfonyl, lower alkylsulfonylamino, and ureido;
$R^1$ is a group selected from the group consisting of hydrogen, hydroxyl, halogen, cyano, nitro, lower alkoxy, amino, carboxyl, and lower alkoxycarbonyl;
$R^2$ is hydrogen or lower alkyl; and
m is an integer of 1 to 3;

or a pharmaceutically acceptable salt thereof.
2) The compound according to the above 1), wherein A is phenyl; or a pharmaceutically acceptable salt thereof.
3) The compound according to the above 1), wherein A is pyridyl or 1-oxypyridyl; or a pharmaceutically acceptable salt thereof.
4) A compound, or a pharmaceutically acceptable salt thereof, which is selected from the group consisting of
3-benzyl-5-phenyl-1H-pyrazolo[4,3-c][1,8]-naphthyridin-4 (5H)-one, 5-phenyl-3-[2-(1-oxypyridin-4-yl)ethyl]-1H-pyrazolo[4,3-c][1,8]-naphthyridin-4 (5H)-one,
5-(3-nitrophenyl)-3-[2-(pyridin-4-yl)ethyl]-1H-pyrazolo[4,3-c][1,8]-naphthyridin-4 (5H)-one,
3-(4-fluorobenzyl)-5-phenyl-1H-pyrazolo[4,3-c][1,8]-naphthyridin-4 (5H)-one,
3-(4-carboxymethylbenzyl)-5-phenyl-1H-pyrazolo[4,3-c][1,8]naphthyridin-4 (5H)-one,
3-(2-methoxybenzyl)-5-phenyl-1H-pyrazolo[4,3-c][1,8]naphthyridin-4 (5H)-one,
3-(2-nitrobenzyl)-5-phenyl-1H-pyrazolo[4,3-c][1,8] naphthyridin-4 (5H)-one,
3-(2,5-dimethoxybenzyl)-5-phenyl-1H-pyrazolo[4,3-c][1,8]naphthyridin-4 (5H)-one,
3-(4-ethoxycarbonylmethylbenzyl)-5-phenyl-1H-pyrazolo[4,3-c][1,8]naphthyridin-4 (5H)-one,
3-benzyl-5-(3-cyanophenyl)-1H-pyrazolo[4,3-c][1,8] naphthyridin-4 (5H)-one,
3-benzyl-5-(3-nitrophenyl)-1H-pyrazolo[4,3-c][1,8] naphthyridin-4 (5H)-one, and
3-benzyl-5-(3-fluorophenyl)-1H-pyrazolo[4,3-c][1,8] naphthyridin-4 (5H)-one.
5) A pharmaceutical composition which comprises an effective amount of a compound according to any of the above 1) to 4) or a pharmaceutically acceptable salt thereof in admixture with a pharmaceutically acceptable carrier.
6) A phosphodiesterase IV inhibitor comprising an effective amount of a compound according to any of the above 1) to 4) or a pharmaceutically acceptable salt thereof.
7) A drug for the prophylaxis and/or treatment of at least one member selected from diseases or abnormal conditions directly or indirectly related to phosphodiesterase IV, said drug comprising an effective amount of a compound according to any of the above 1) to 4) or a pharmaceutically acceptable salt thereof.
8) A drug comprising an effective amount of a compound according to any of the above 1) to 4) or a pharmaceutically acceptable salt thereof,
said drug for preventing and/or treating at least one respiratory disease selected from the group consisting of:
bronchial asthma including chronic bronchial asthma and atopic asthma; acute bronchitis; chronic bronchitis; asthmatic bronchitis; pneumonic diseases; pulmonary emphysema; chronic obstructive pulmonary disease (COPD); and acute respiratory distress syndrome (ARDS).
9) An anti-asthmatic comprising an effective amount of a compound according to any of the above 1) to 4) or a pharmaceutically acceptable salt thereof.

The aforementioned diseases or abnormal conditions directly or indirectly related to phosphodiesterase IV may include, for example, the following:
(1) inflammatory diseases, including atopic dermatitis, conjunctivitis, urticaria, acquired immunodeficiency syndrome (AIDS), keloid formation, rhinitis, iridocyclitis, gingivitis, periodontitis, dentoalveolitis, gastritis, ulcerative colitis, Crohn's disease, gastrointestinal ulcer, esophagitis, myositis, encephalitis, myasthenia gravis, multiple sclerosis, neuritis, hepatitis, scar tissue formation, nephritis (including proliferative nephritis), peritonitis, pleurisy, scleritis, scleroderma, scalds or burns, and the like;

(2) systemic or local joint diseases, including osteoarthritis, gouty arthritis, rheumatoid arthritis, malignant rheumatism, psoriatic arthritis, and the like;

(3) inflammatory conditions associated with organ transplantation, etc., including reperfusion injury, graft versus host reaction, and the like;

(4) diseases related to urination, including diabetes insipidus, urethritis, urinary incontinence, cystitis, irritable bladder, neurogenic bladder, uremia, uriniferous tubular disorder, pollakiuria, ischuria, and the like;

(5) diseases or abnormal conditions related to tumor necrosis factor (TNF) (for example, TNF-α, etc.) and other cytokines (for example, IL-1, IL-4, IL-6, etc.), including psoriasis, rheumatoid arthritis, ulcerative colitis, Crohn's disease, septicemia, septic shock, endotoxic shock, gram negative *bacillus* sepsis, toxic shock syndrome, nephritis, hepatitis, infection (induced by bacteria and viruses), circulatory failure (heart failure, arteriosclerosis, myocardial infarction, cerebral apoplexy), and the like;

(6) proliferative diseases, including malignant tumors, leukemia, proliferative dermal diseases (keratosis and various types of dermatitides), connective tissue diseases and the like;

(7) diseases related to nervous function abnormality, including impaired learning, memory and recognition related to neurodegenerative disorders such as Alzheimer's disease and Parkinson's disease, multiple lateral sclerosis, senile dementia, amyotrophic lateral sclerosis, acute demyelinating neuritis, muscular dystrophy, and the like;

(8) diseases related to abnormality of mental functions, including manic-depressive psychosis, schizoid, anxiety, panic, and the like;

(9) diseases demanding protection of nerves and cells, including cardiac arrest, spinal cord injury, intermittent claudication, ischemic diseases (including angina pectoris, cardiac infarction, cerebral apoplexy, head injury, etc.) and the like;

(10) endocrine diseases, including not only diabetes but also diabetic retinopathy, diabetic nephropathy, diabetic neurosis, amyloidosis, pancreatitis, thyroiditis, obesity, prostatomegaly, and the like;

(11) autoimmune diseases, including systemic lupus erythematosus (SLE), atrophic gastritis, thyroid diseases, glomerular nephritis, orchitis, adrenal diseases, hemolytic anemia, oophoritis, and the like;

(12) cardiovascular diseases, including hypertension, angina pectoris, heart failure, myocarditis, external epicarditis, endocarditis, valvulitis, and the like;

(13) vessel and blood system diseases, including angiitis, aneurysm, endoangiosis, thromboangiitis, granulomatosis, cerebrovascular angiitis, arteriosclerosis, periangitis, leukopenia, thrombocytopenia, Boeck's sarcoid, and the like;

(14) diseases related to immune reactions or allergic responses, including contact dermatitis, serum sickness, drug allergy, Goodpasture's syndrome, lymphoma, rheumatic fever, AIDS, anaphylactic shock and the like; and

(15) other diseases, disorders or abnormal states, including glaucoma, spastic paralysis, impotence, diseases or illness accompanied with pain (contusion, headache, etc.), neck-shoulder-arm syndrome, nephropathy, renal insufficiency, hepatic insufficiency, obesity, female sterility, alopecia, etc.

ADVANTAGEOUS EFFECTS BY THE PRESENT INVENTION

The present invention can provide PDE IV inhibitors. The instant inventive compounds have excellently potent inhibitory action toward PDE IV. The inventive compounds inhibit PDE IV predominantly present in airway smooth muscle cells and inflammatory cells, allowing the elevation of cAMP levels in said cells in order to relax the airway smooth muscles and simultaneously suppress the activation of inflammatory cells. Further, since it is perceivable that there is a great difference between dose levels for pharmacological actions and those for inhibition of drug metabolizing enzymes in the inventive compounds, it is considered that the present invention allows the production of excellently pharmacologically-effective and highly safe anti-asthmatic agents and prophylactic and/or therapeutic agents for COPD.

The above objectives and other objectives, features, advantages, and aspects of the present invention are readily apparent to those skilled in the art from the following disclosures. It should be understood, however, that the description of the specification including the following best modes of carrying out the invention, examples, etc. is illustrating preferred embodiments of the present invention and given only for explanation thereof. It will become apparent to the skilled in the art that a great number of variations and/or alterations (or modifications) of this invention may be made based on knowledge from the disclosure in the following parts and other parts of the specification without departing from the spirit and scope thereof as disclosed herein. All of the patent publications and reference documents listed herein for illustrative purposes are hereby incorporated by reference into the present disclosure.

BEST MODES OF CARRYING OUT THE INVENTION

The present invention provides PDE IV-inhibitory pyrazolo[4,3-c][1,8]naphthyridin-4 (5H)-one derivatives (1), or salts thereof, having an unsubstituted or optionally substituted phenyl, pyridyl, 1-oxypyridyl or thienyl group via 1 to 3 methylene chains on the 3 position of the pyrazolo[4,3-c][1, 8]naphthyridin-4 (5H)-one ring which may be unsubstituted or optionally substituted on the 1 position thereof, and pharmaceutical compositions comprising at least one member selected from the aforementioned compounds and pharmaceutically acceptable salts thereof. The present invention also provides potent drugs with advantageous actions.

The definitions for the compounds of the above-defined formula (1) will be given below in detail.

The term "halogen" as used herein refers to fluorine, chlorine, bromine, and the like.

The term "lower alkyl" refers to alkyl containing 1 to 4 carbon atoms, such as methyl, ethyl, propyl, isopropyl, n-butyl, i-butyl, sec-butyl and t-butyl.

The term "lower alkoxy" refers to alkoxy containing 1 to 4 carbon atoms, such as methoxy, ethoxy, propoxy, isopropoxy, n-butoxy, i-butoxy, sec-butoxy and t-butoxy.

The term "lower alkylcarbonyloxy" refers to alkylcarbonyloxy containing 2 to 5 carbon atoms, such as acetoxy, ethylcarbonyloxy, propylcarbonyloxy, isopropylcarbonyloxy, n-butylcarbonyloxy, isobutylcarbonyloxy, sec-butylcarbonyloxy and t-butylcarbonyloxy.

The term "lower alkoxycarbonyl" refers to alkoxycarbonyl containing 2 to 5 carbon atoms, such as methoxycarbonyl, ethoxycarbonyl, propoxycarbonyl, isopropoxycarbonyl, n-butoxycarbonyl, isobutoxycarbonyl, sec-butoxycarbonyl and t-butoxycarbonyl.

The term "carboxy-lower alkylene" refers to carboxy-lower alkylene constituted of carboxy in combination with straight-chain alkylene containing 1 to 4 carbon atoms, such as carboxymethylene, carboxyethylene, carboxytrimethylene, and carboxytetramethylene.

The term "lower alkoxycarbonyl-lower alkylene" refers to alkoxycarbonyl-lower alkylene constituted of alkoxycarbonyl containing 2 to 5 carbon atoms in combination with straight-chain alkylene containing 1 to 4 carbon atoms, such as methoxycarbonylmethylene, ethoxycarbonylmethylene, propoxycarbonylmethylene, isopropoxycarbonylmethylene, n-butoxycarbonylmethylene, isobutoxycarbonylmethylene, sec-butoxycarbonylmethylene, t-butoxycarbonylmethylene, methoxycarbonylethylene, ethoxycarbonylethylene, propoxycarbonylethylene, isopropoxycarbonylethylene, n-butoxycarbonylethylene, isobutoxycarbonylethylene, sec-butoxycarbonylethylene, t-butoxycarbonylethylene, methoxycarbonyltrimethylene, ethoxycarbonyltrimethylene, propoxycarbonyltrimethylene, isopropoxycarbonyltrimethylene, n-butoxycarbonyltrimethylene, isobutoxycarbonyltrimethylene, sec-butoxycarbonyltrimethylene, t-butoxycarbonyltrimethylene, methoxycarbonyl-tetramethylene, ethoxycarbonyltetramethylene, propoxycarbonyltetramethylene, isopropoxycarbonyltetramethylene, n-butoxycarbonyltetramethylene, isobutoxycarbonyltetramethylene, sec-butoxycarbonyltetramethylene, and t-butoxycarbonyltetramethylene.

The term "lower alkylsulfonyl" refers to alkylsulfonyl containing 1 to 4 carbon atoms, such as methylsulfonyl, ethylsulfonyl, propylsulfonyl, isopropylsulfonyl, n-butylsulfonyl, isobutylsulfonyl, sec-butylsulfonyl and t-butylsulfonyl.

The term "lower alkylsulfonylamino" refers to alkylsulfonylamino containing 1 to 4 carbon atoms, such as methylsulfonylamino, ethylsulfonylamino, propylsulfonylamino, isopropylsulfonylamino, n-butylsulfonylamino, isobutylsulfonylamino, sec-butylsulfonylamino and t-butylsulfonylamino.

Representative examples of compounds of the invention include the following:
- 5-phenyl-3-[2-(pyridin-4-yl)ethyl]-1H-pyrazolo[4,3-c][1,8]-naphthyridin-4 (5H)-one
- 1-methyl-5-phenyl-3-[2-(pyridin-4-yl)ethyl]-1H-pyrazolo[4,3-c][1,8]-naphthyridin-4 (5H)-one
- 5-phenyl-3-[2-(pyridin-3-yl)ethyl]-1H-pyrazolo[4,3-c][1,8]-naphthyridin-4 (5H)-one
- 5-phenyl-3-(pyridin-3-yl)methyl-1H-pyrazolo[4,3-c][1,8]-naphthyridin-4 (5H)-one
- 5-phenyl-3-[2-(1-oxypyridin-4-yl)ethyl]-1H-pyrazolo[4,3-c][1,8]-naphthyridin-4 (5H)-one
- 5-(3-nitrophenyl)-3-[2-(pyridin-4-yl)ethyl]-1H-pyrazolo[4,3-c][1,8]-naphthyridin-4 (5H)-one
- 5-(3-nitrophenyl)-3-[2-(1-oxypyridin-4-yl)ethyl]-1H-pyrazolo[4,3-c][1,8]-naphthyridin-4 (5H)-one
- 5-(3-aminophenyl)-3-[2-(pyridin-4-yl)ethyl]-1H-pyrazolo[4,3-c][1,8]-naphthyridin-4 (5H)-one
- 3-benzyl-5-phenyl-1H-pyrazolo[4,3-c][1,8]-naphthyridin-4 (5H)-one
- 5-phenyl-3-(2-phenylethyl)-1H-pyrazolo[4,3-c][1,8]-naphthyridin-4 (5H)-one
- 3-[2-(4-nitrophenyl)ethyl]-5-phenyl-1H-pyrazolo[4,3-c][1,8]-naphthyridin-4 (5H)-one
- 3-[2-(4-cyanophenyl)ethyl]-5-phenyl-1H-pyrazolo[4,3-c][1,8]-naphthyridin-4 (5H)-one
- 3-[2-(4-aminophenyl)ethyl]-5-phenyl-1H-pyrazolo[4,3-c][1,8]naphthyridin-4 (5H)-one
- 3-[2-(4-carboxyphenyl)ethyl]-5-phenyl-1H-pyrazolo[4,3-c][1,8]naphthyridin-4 (5H)-one
- 3-[2-(3-nitrophenyl)ethyl]-5-phenyl-1H-pyrazolo[4,3-c][1,8]naphthyridin-4 (5H)-one
- 3-[2-(2-nitrophenyl)ethyl]-5-phenyl-1H-pyrazolo[4,3-c][1,8]naphthyridin-4 (5H)-one
- 3-[2-(2-cyanophenyl)ethyl]-5-phenyl-1H-pyrazolo[4,3-c][1,8]naphthyridin-4 (5H)-one
- 3-[2-(3-cyanophenyl)ethyl]-5-phenyl-1H-pyrazolo[4,3-c][1,8]naphthyridin-4 (5H)-one
- 3-[2-(4-methylphenyl)ethyl]-5-phenyl-1H-pyrazolo[4,3-c][1,8]naphthyridin-4 (5H)-one
- 3-(3-methoxybenzyl)-5-phenyl-1H-pyrazolo[4,3-c][1,8]naphthyridin-4 (5H)-one
- 3-(4-methoxybenzyl)-5-phenyl-1H-pyrazolo[4,3-c][1,8]-naphthyridin-4 (5H)-one
- 3-(2-methoxybenzyl)-5-phenyl-1H-pyrazolo[4,3-c][1,8]-naphthyridin-4 (5H)-one
- 3-(2-thienylmethyl)-5-phenyl-1H-pyrazolo[4,3-c][1,8]-naphthyridin-4 (5H)-one
- 3-(4-nitrobenzyl)-5-phenyl-1H-pyrazolo[4,3-c][1,8]-naphthyridin-4 (5H)-one
- 3-(3-nitrobenzyl)-5-phenyl-1H-pyrazolo[4,3-c][1,8]-naphthyridin-4 (5H)-one
- 3-(2-nitrobenzyl)-5-phenyl-1H-pyrazolo[4,3-c][1,8]-naphthyridin-4 (5H)-one
- 3-(2,5-dimethoxybenzyl)-5-phenyl-1H-pyrazolo[4,3-c][1,8]-naphthyridin-4 (5H)-one
- 3-(3,4-dimethoxybenzyl)-5-phenyl-1H-pyrazolo[4,3-c][1,8]-naphthyridin-4 (5H)-one
- 3-(3,5-dimethoxybenzyl)-5-phenyl-1H-pyrazolo[4,3-c][1,8]-naphthyridin-4 (5H)-one
- 3-(2,4-dimethoxybenzyl)-5-phenyl-1H-pyrazolo[4,3-c][1,8]naphthyridin-4 (5H)-one
- 3-(4-cyanobenzyl)-5-phenyl-1H-pyrazolo[4,3-c][1,8]-naphthyridin-4 (5H)-one
- 3-(4-ethoxycarbonylmethylbenzyl)-5-phenyl-1H-pyrazolo[4,3-c][1,8]naphthyridin-4 (5H)-one
- 3-(4-fluorobenzyl)-5-phenyl-1H-pyrazolo[4,3-c][1,8]-naphthyridin-4 (5H)-one
- 3-(4-methylsulfonylbenzyl)-5-phenyl-1H-pyrazolo[4,3-c][1,8]naphthyridin-4 (5H)-one
- 3-[2-(3-aminophenyl)ethyl]-5-phenyl-1H-pyrazolo[4,3-c][1,8]naphthyridin-4 (5H)-one
- 3-[2-(2-aminophenyl)ethyl]-5-phenyl-1H-pyrazolo[4,3-c][1,8]naphthyridin-4 (5H)-one
- 3-[2-(2-carboxyphenyl)ethyl]-5-phenyl-1H-pyrazolo[4,3-c][1,8]naphthyridin-4 (5H)-one
- 3-[2-(3-carboxyphenyl)ethyl]-5-phenyl-1H-pyrazolo[4,3-c][1,8]naphthyridin-4 (5H)-one
- 3-(4-carboxybenzyl)-5-phenyl-1H-pyrazolo[4,3-c][1,8]-naphthyridin-4 (5H)-one
- 3-(3-hydroxybenzyl)-5-phenyl-1H-pyrazolo[4,3-c][1,8]-naphthyridin-4 (5H)-one
- 3-(4-hydroxybenzyl)-5-phenyl-1H-pyrazolo[4,3-c][1,8]-naphthyridin-4 (5H)-one
- 3-(2-hydroxybenzyl)-5-phenyl-1H-pyrazolo[4,3-c][1,8]-naphthyridin-4 (5H)-one
- 3-(4-aminobenzyl)-5-phenyl-1H-pyrazolo[4,3-c][1,8]-naphthyridin-4 (5H)-one
- 3-(3-aminobenzyl)-5-phenyl-1H-pyrazolo[4,3-c][1,8]-naphthyridin-4 (5H)-one
- 3-(2-aminobenzyl)-5-phenyl-1H-pyrazolo[4,3-c][1,8]-naphthyridin-4 (5H)-one 3-(4-carboxymethylbenzyl)-5-phenyl-1H-pyrazolo[4,3-c][1,8]naphthyridin-4 (5H)-one
3-(4-acetoxybenzyl)-5-phenyl-1H-pyrazolo[4,3-c][1,8]naphthyridin-4 (5H)-one
3-[2-(4-methanesulfonylaminophenyl)ethyl]-5-phenyl-1H-pyrazolo[4,3-c][1,8]naphthyridin-4 (5H)-one
3-(4-methanesulfonylaminobenzyl)-5-phenyl-1H-pyrazolo[4,3-c][1,8]naphthyridin-4 (5H)-one
5-phenyl-3-[2-(2-ureidophenyl)ethyl]-1H-pyrazolo[4,3-c][1,8]naphthyridin-4 (5H)-one
3-benzyl-5-(4-methoxyphenyl)-1H-pyrazolo[4,3-c][1,8]naphthyridin-4 (5H)-one
3-benzyl-5-(4-hydroxyphenyl)-1H-pyrazolo[4,3-c][1,8]naphthyridin-4 (5H)-one
3-benzyl-5-(3-cyanophenyl)-1H-pyrazolo[4,3-c][1,8]naphthyridin-4 (5H)-one
3-benzyl-5-(3-carboxyphenyl)-1H-pyrazolo[4,3-c][1,8]naphthyridin-4 (5H)-one
5-phenyl-3-(3-phenylpropyl)-1H-pyrazolo[4,3-c][1,8]naphthyridin-4 (5H)-one
3-benzyl-5-(3-nitrophenyl)-1H-pyrazolo[4,3-c][1,8]naphthyridin-4 (5H)-one
5-(3-aminophenyl)-3-benzyl-1H-pyrazolo[4,3-c][1,8]naphthyridin-4 (5H)-one
3-benzyl-5-(3-fluorophenyl)-1H-pyrazolo[4,3-c][1,8]naphthyridin-4 (5H)-one As used herein, "the compound(s) of the present invention" may include salts thereof, hydrates and solvates thereof, a variety of prodrug forms derived from functional groups existing in compound molecules. The prodrugs of the compounds according to the present invention include those compounds which can be transformed in vivo, for example, by metabolic processes, including hydrolysis, oxidation, reduction, trans-esterification, and the like, to yield the parent compounds of the formula (1), etc. Representatives of such prodrugs are ester-, ether-, amide-, alcohol-, and amine-derivatives thereof. Preferred compounds according to the present invention have specific inhibitory properties against PDE IV.

Some of the compounds of the present invention may exist in more than one tautomeric form. This invention extends to all tautomeric forms. The compounds of the instant invention may also contain one or plural asymmetric carbon atoms and thus give rise to optical isomers such as (R)- and (S)-isomers, racemates, diastereoisomers, etc. The present invention includes all such possible isomers, and their racemic and resolved, enantiomerically pure forms, as well as all mixtures thereof.

Examples of the aforementioned tautomers include a compound of the following general formula (1-a) wherein A, m and $R^1$ have the same meanings as defined above, and a compound of the following general formula (1-b) wherein A, m and $R^1$ have the same meanings as defined above:

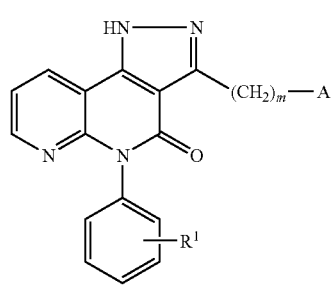

(1-a)

-continued

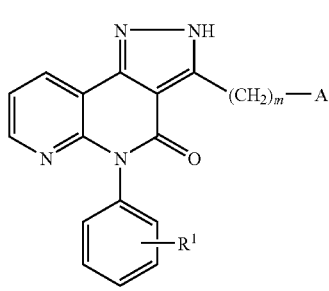

(1-b)

The compounds of the invention may be isolated in the form of hydrates, solvates with, for example, ethanol and the like, and a variety of crystalline substances.

The present invention also encompasses pharmaceutically acceptable salts of the naphthyridine derivative having the formula (1). Such salts include those formed from any of medically or pharmaceutically utilizable non-toxic or low toxic inorganic or organic acids and bases. Examples of the salts are hydrochloride, hydrobromate, sulfate, acetate, propionate, citrate, succinate, tartrate, methanesulfonate, p-toluenesulfonate, etc.; and alkali metal salts (e.g., sodium salts, potassium salts), alkali earth metal salts (e.g., calcium salts, magnesium salts), ethylene diamine salts, etc.

The compounds of the present invention can be prepared by one of various routes. For instance, the compounds of the formula (1) can be prepared by one of the following schemes or modifications thereof:

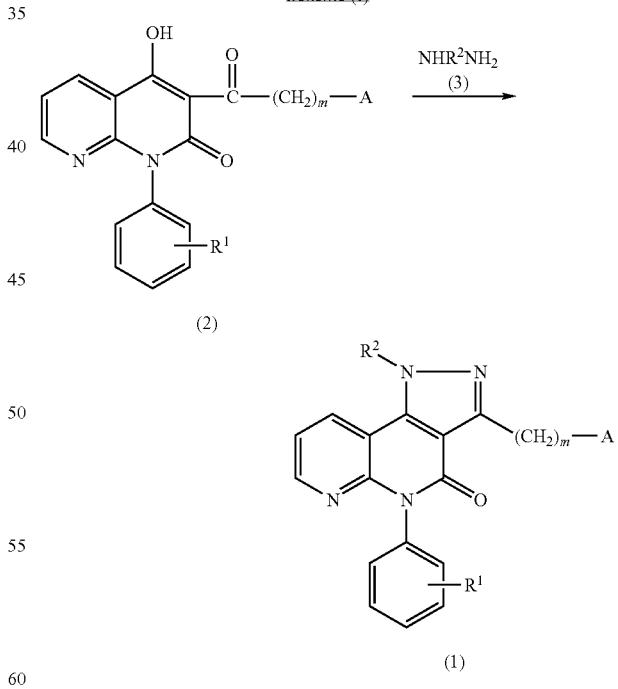

Briefly, the compounds of the formula (1) wherein A, m, $R^1$ and $R^2$ have the meanings given above can be prepared by condensing a compound of the formula (2) wherein A, m, and $R^1$ have the meanings given above with a compound of the formula (3) wherein $R^2$ has the meaning given above, or a hydrate or salt thereof. The reaction can be conducted in the presence of or in the absence of a solvent. When the reaction is conducted in solvents, it is often convenient to use conventional solvents which are free from any adverse action on the reaction. Examples of such solvents are methanol, ethanol, isopropyl alcohol, acetic acid, propionic acid, diethyl ether, tetrahydrofuran (THF), chloroform, dichloromethane, dimethyl sulfoxide, N,N-dimethylformamide, N,N-diphenylformamide, sulfolane, etc. Preferred examples of such solvents are ethanol, N,N-dimethylformamide, acetic acid, etc. The reaction temperature range is about 0° C. to 200° C. and preferably room temperature to about 160° C.

The compounds, wherein the substituent group on the phenyl, pyridyl, 1-oxypyridyl, or thienyl group for A is selected from the group consisting of hydroxyl, acetoxy, amino, carboxyl, carboxy-lower alkylene and lower alkylsulfonylamino, can be derived from the compound of the formula (1) by hydrolysis, oxidation, reduction or one of other various conventional methods which the artisan in the art can utilize. The compounds wherein $R^1$ is hydroxyl, amino or carboxyl can be derived from the compound of the formula (1) by one of various conventional methods which the artisan in the art can utilize.

In the aforementioned Scheme (I), the compounds of the formula (2) can be prepared according to one of the following scheme (II) and modifications thereof:

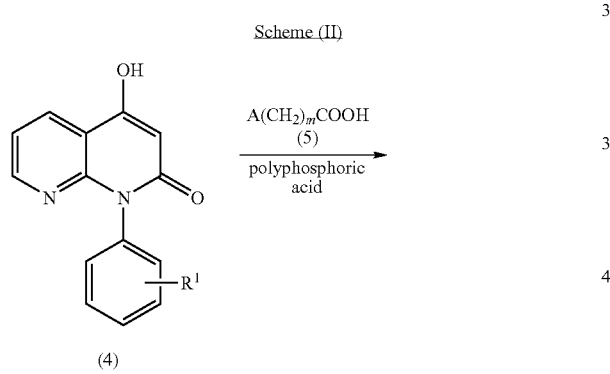

Briefly, a compound of the formula (4) wherein $R^1$ has the meaning given above can react with a compound of the formula (5) wherein A and m have the meanings given above in the presence of polyphosphoric acid to produce the compound of the formula (2).

The compounds of the formula (2) can be prepared according to one of the following scheme (III) and modifications thereof:

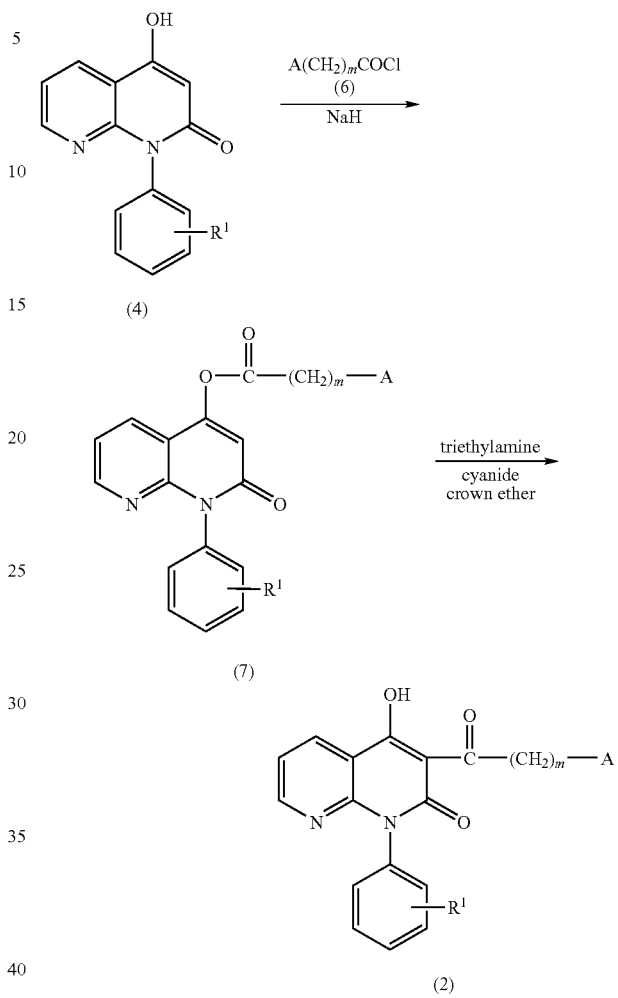

Briefly, a compound of the formula (4) wherein $R^1$ has the meaning given above can react with a compound of the formula (6) wherein A and m have the meanings given above in the presence of sodium hydride to produce a compound of the formula (7). Next, the resulting compound of the formula (7) can be treated with a cyanide such as lithium cyanide, sodium cyanide and potassium cyanide, a base such as triethylamine, in the presence of crown ether such as 15-crown-5 ether, 12-crown-4 ether and 18-crown-6 ether, in a solvent such as toluene, to produce the compound of the formula (2).

In the aforementioned Scheme (III), a compound of the formula (4) can react with a compound of the formula (6) wherein m=1 in the presence of sodium hydride at an excess equivalent (preferably 2 to 3 equivalents) to produce directly the compound of the formula (2) without passing through the compound of the formula (7).

In the aforementioned Schemes (II) and (III), the compounds of the formula (4) can be prepared by one of known methods (e.g., JP, A, 61-246183 (1986); J. Med. Chem., 31, 2108 (1988)) or modifications thereof.

The compounds of the formula (4) can be prepared by one of the following Scheme (IV) and modifications thereof:

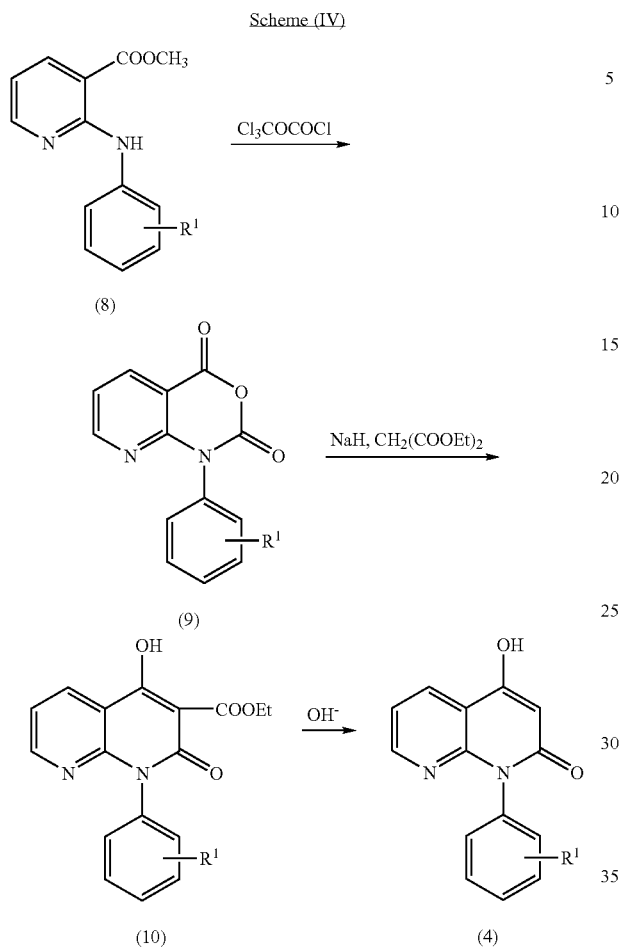

Briefly, a compound of the formula (8) can be converted according to one of modifications of known methods (JP, A, 5-194515 (1993)) into a compound of the formula (10) wherein R¹ has the meaning given above via a compound of the formula (9). Next, the compound of the formula (10) can react with alkali metal hydroxide, or alkali earth metal hydroxide, (for example, potassium hydroxide) to produce the compound of the formula (4). In the aforementioned Scheme (IV), the compounds of the formula (8) can be prepared by one of known methods (e.g., WO, A, 01/42244) or modifications thereof.

The compounds of the present invention are potent PDE IV inhibitors. The compounds of the present invention are thus of use in the prophylaxis and treatment of diseases and abnormal states directly or indirectly related to PDE IV actions. In particular, the compounds of the present invention are effective as prophylactic or therapeutic agents for diseases and conditions associated with an abnormal enzymatic or catalytic activity of PDE IV. The compounds of the present invention are useful as prophylactic or therapeutic agents or drugs for especially the prophylaxis and treatment of:

(1) respiratory diseases, including, for example, bronchial asthma (including chronic bronchial asthma and atopic asthma), acute bronchitis, chronic bronchitis, asthmatic bronchitis, pneumonic diseases, pulmonary emphysema, chronic obstructive pulmonary disease (COPD), acute respiratory distress syndrome (ARDS), and the like;

(2) inflammatory diseases, including, for example, atopic dermatitis, conjunctivitis, urticaria, acquired immunodeficiency syndrome (AIDS), keloid formation, rhinitis, iridocyclitis, gingivitis, periodontitis, dentoalveolitis, gastritis, ulcerative colitis, Crohn's disease, gastrointestinal ulcer, esophagitis, myositis, encephalitis, myasthenia gravis, multiple sclerosis, neuritis, hepatitis, scar tissue formation, nephritis (including proliferative nephritis), peritonitis, pleurisy, scleritis, scleroderma, scalds or burns, and the like;

(3) systemic or local joint diseases, including, for example, osteoarthritis, gouty arthritis, rheumatoid arthritis, malignant rheumatism, psoriatic arthritis, and the like;

(4) inflammatory conditions associated with organ transplantation, etc., including, for example, reperfusion injury, graft versus host reaction, and the like;

(5) diseases or symptoms related to urination, including, for example, diabetes insipidus, urethritis, urinary incontinence, cystitis, irritable bladder, neurogenic bladder, uremia, uriniferous tubular disorder, pollakiuria, ischuria, and the like;

(6) diseases or abnormal conditions related to, for example, tumor necrosis factor (TNF) (TNF-α, etc.) and other cytokines (for example, IL-1, IL-4, IL-6, etc.), including psoriasis, rheumatoid arthritis, ulcerative colitis, Crohn's disease, septicemia, septic shock, endotoxic shock, gram-negative *bacillus* sepsis, toxic shock syndrome, nephritis, hepatitis, infection (induced by bacteria and viruses), circulatory failure (heart failure, arteriosclerosis, myocardial infarction, cerebral apoplexy), and the like;

(7) proliferative diseases, including, for example, malignant tumors, leukemia, proliferative dermal diseases (keratosis and various types of dermatitides), connective tissue diseases and the like;

(8) diseases related to nervous function abnormality, including, for example, impaired learning, memory and recognition associated with neurodegenerative disorders such as Alzheimer's disease and Parkinson's disease, multiple lateral sclerosis, senile dementia, amyotrophic lateral sclerosis, acute demyelinating neuritis, muscular dystrophy, and the like;

(9) diseases related to abnormality of mental functions, including, for example, manic-depressive psychosis, schizoid, anxiety, panic, and the like;

(10) diseases demanding protection of nerves and cells, including, for example, cardiac arrest, spinal cord injury, intermittent claudication, ischemic diseases (including angina pectoris, cardiac infarction, cerebral apoplexy, head injury, etc.) and the like;

(11) endocrine diseases, including not only diabetes but also diabetic retinopathy, diabetic nephropathy, diabetic neurosis, amyloidosis, pancreatitis, thyroiditis, obesity, prostatomegaly, and the like;

(12) autoimmune diseases, including, for example, systemic lupus erythematosus (SLE), atrophic gastritis, thyroid diseases, glomerular nephritis, orchitis, adrenal diseases, hemolytic anemia, oophoritis, and the like;

(13) cardiovascular diseases, including, for example, hypertension, angina pectoris, heart failure, myocarditis, external epicarditis, endocarditis, valvulitis, and the like;

(14) vessel and blood system diseases, including, for example, angiitis, aneurysm, endoangiosis, thromboangiitis, granulomatosis, cerebrovascular angiitis, arteriosclerosis, periangitis, leukopenia, thrombocytopenia, Boeck's sarcoid, and the like;

(15) diseases related to immune reactions or allergic responses, including, for example, contact dermatitis, serum sickness, drug allergy, Goodpasture's syndrome, lymphoma, rheumatic fever, AIDS, anaphylactic shock and the like; and

(16) other diseases, disorders or abnormal states, including, for example, glaucoma, spastic paralysis, impotence, diseases or illness accompanied with pain (contusion, headache, etc.), neck-shoulder-arm syndrome, nephropathy, renal insufficiency, hepatic insufficiency, obesity, female sterility, alopecia, etc.

It is known that the aforementioned diseases and abnormal conditions would be or are directly or indirectly related to PDE IV.

Particularly, the compounds of the present invention act as prophylactic and/or therapeutic drugs for:

(i) respiratory diseases (such as bronchial asthma including chronic bronchial asthma and atopic asthma; acute bronchitis; chronic bronchitis; asthmatic bronchitis; pneumonic diseases; pulmonary emphysema; chronic obstructive pulmonary disease (COPD); acute respiratory distress syndrome (ARDS); etc.); and (ii) inflammatory diseases (such as atopic dermatitis; conjunctivitis; urticaria; acquired immunodeficiency syndrome (AIDS); keloid formation; rhinitis; iridocyclitis; gingivitis; periodontitis; dentoalveolitis; gastritis; ulcerative colitis; Crohn's disease; gastrointestinal ulcer; esophagitis; myositis; encephalitis (such as myasthenia gravis, multiple sclerosis and neuritis); hepatitis; scar tissue formation; nephritis including proliferative nephritis; peritonitis; pleurisy; scleritis; scleroderma; scalds or burns; etc.)

Among them, the compounds of the present invention are most preferably effective as prophylactic and/or therapeutic drugs for bronchial asthma and COPD.

It is also verified that the compounds of the present invention are significantly less inhibitory toward drug-metabolizing enzymes such as CYP2D6 and CYP3A4 than the prior art PDE IV inhibitors. In other words, as illustrated herein below in assay examples, the prior art PDE IV inhibitors have a slight difference between their pharmacologically-effective dose (such as anti-asthmatic dose) and their effective dose for inhibiting drug-metabolizing enzymes, or inhibit drug-metabolizing enzymes at a less dose than they exert a pharmaceutical action, etc., whereby it is anxious to limit their clinical applications. In contrast, the compounds of the present invention have unexpectedly much higher dose levels for inhibitory action on the drug-metabolizing enzymes than for pharmacological action, and extremely advantageous in view of safety.

Thus, the present invention encompasses pharmaceutical compositions comprising an effective amount of at least one member selected from the above-defined compounds (1) and pharmaceutically acceptable salts thereof, including not only PDE IV-specific inhibitors but also anti-asthmatic agents and prophylactic or therapeutic agents for COPD.

As aforementioned, since PDE IV is predominantly in vivo located in airway smooth muscle cells and inflammatory cells, the compounds of the present invention inhibit PDE IV in these cells, thereby exerting a bronchodilator action via relaxing airway smooth muscles, together with an anti-inflammatory action through suppressing inflammatory cell activation. Hence, the compounds of the present invention are widely effective in ameliorating a variety of undesirable responses and symptoms raised with regard to asthma and COPD.

The following disclosure is to illustrate an anti-asthmatic action, one of actions produced by the compounds of the present invention in detail:

It is known that a series of responses, such as an immediate asthmatic response, a delayed asthmatic response, and a hypersensitive airway response, are induced when an asthmatic patient inhales antigens which cause the disease.

First, the immediate asthmatic response that begins immediately after inhalation of antigens is a typical airway smooth muscle constrictive reaction induced by chemical mediators (including histamine, leukotrienes, etc.) which are released from mast cells as a result of antigen-antibody interactions. Later the delayed asthmatic response is observed, which occurs within 4 to 24 hours after the inhalation of antigens. For its pathological states, an infiltration of inflammatory cells into lung tissues, airway mucosa edema, etc. are observed. Thereafter, the hypersensitive airway response is further elicited, which occurs within 1 to 14 days after the inhalation of antigens and is a state wherein the airway reactivity is increased. In such a stage, even quite mild stimuli lead to constriction of the airway and occurrence of serious airway obstruction.

As aforementioned, various responses and symptoms appear in asthma. The compounds of the present invention can exert an excellent inhibitory and/or ameliorating activity on such responses and symptoms at each stage, relying on their bronchodilator and anti-inflammatory actions based on the inhibition of PDE IV.

Diseases and abnormal states to be targeted by the therapy using the compounds of the present invention include the aforementioned diseases and abnormal conditions, preferably diseases and abnormal conditions accompanied with respiratory dysfunctions and inflammation at the area of bronchus and airway. Embodiments of such diseases include bronchial asthma including chronic bronchial asthma and atopic asthma, acute bronchitis, chronic bronchitis, asthmatic bronchitis, pneumonic diseases, pulmonary emphysema, chronic obstructive pulmonary disease (COPD), acute respiratory distress syndrome (ARDS), and other bronchus and airway inflammatory states, etc.

For patients with the foregoing diseases, disorders, and abnormal states, the compounds of the present invention can be used independently without any additives, but preferably in admixture with any of pharmaceutically acceptable additives. The compounds of the present invention may be orally, parenterally (including by injection), topically (including by inhalation) administered as pharmaceutical compositions or formulations. One or more components selected from known pharmaceutical additives (hereinafter also referred to "pharmaceutical ingredient(s)") can be employed in the aforementioned pharmaceutical compositions or formulations for any of administration routes. Embodiments of such known pharmaceutical additives may be suitably selected, according to administration routes and applications of pharmaceutically formulated forms, from components as disclosed in, for example, (1) "Iyakuhin Tenkabutsu Handbook (Handbook of PHARMACEUTICAL EXCIPIENTS)", Maruzen Publishing Company, Japan (1989); (2) "Iyakuhin Tenkabutsu Jiten (Pharmaceutical Excipient Dictionary)", First Edition, K.K. Yakuji Nippo Sha, Japan (1994); (3) "Iyakuhin Tenkabutsu Jiten Tsuiho (Pharmaceutical Excipient Dictionary, Supplement)", First Edition, K.K. Yakuji Nippo Sha, Japan (1995); and (4) "Yakuzaigaku (Pharmaceutics)", 5th Edition, K.K. Nankodo, Japan (1997).

For oral administration, the aforementioned additives are any pharmaceutical ingredients as long as they are suitable for oral drugs and the intended purposes according to the present invention. Usually, the pharmaceutical additive is selected from conventional pharmaceutical ingredients such as vehicles, binders, disintegrants, lubricants, and coating agents. The oral formulations of the present invention include tablets, capsules, granules, fine granules, powders, syrups, etc. The oral drug includes controlled-release system preparations wherein the in vivo release of the compound of the present invention which is contained as the active ingredient is controlled using any of known pharmaceutical ingredients (for example, immediate-release preparations, sustained-release preparations, etc.).

The aforementioned oral drug may include enteric preparations. In some cases, it is rather preferable that the oral drugs are prepared in the form of such enteric preparations. Such enteric preparations include capsule formulations wherein any of enteric coating agents is contained as an ingredient for their coat, said enteric coating agent being selected from cellulose phthalate, hydroxypropyl methylcellulose phthalate, and methyl methacrylate-methacrylic acid copolymers, etc.

For injection, the additives include pharmaceutical ingredients suitable for aqueous or non-aqueous injections. Usually, the additive is selected from conventional pharmaceutical ingredients such solubilizers, solution adjuvants, suspending agents, buffers (pH regulators), stabilizers and preservatives. In addition, it may be selected from conventional ingredients suitable for preparing powders for injection, which are used in solution or suspension when administered.

When administered topically, for example, via inhalation, etc., the aforementioned additives as used herein include any of pharmaceutical ingredients known in the art, such as solution adjuvants, stabilizers, buffers, suspending agents, emulsifying agents, and preservatives. Embodiments of inhalants include aerosols. Aerosol-producing techniques are any of types including a spraying type wherein active drug ingredients are packed together with propellants such as fluorocarbon alternatives into a sealed container and sprayed, and a nebulizer or atomizer type using a pressured gas, such as carbon dioxide and nitrogen, filled in a container different from that for active drug ingredients.

Desired oral drugs, injections or drugs for topical applications (including inhalants) comprising the compound of the present invention in admixture with the aforementioned ingredient can be prepared according to manufacturing methods known per se, for example, those described in The 14th Pharmacopoeia of Japan (JPXIV) or appropriately modified ones.

The pharmaceutical compositions (drugs) of the present invention are administered to mammals, particularly including human. The doses of these compounds or salts thereof are usually about 0.1 to 1,000 mg (per day), preferably about 0.1 to 500 mg (per day) for oral administration; usually about 0.01 to 200 mg (per day), preferably about 0.05 to 100 mg (per day) for injection; and usually about 0.01 to 200 mg (per day), preferably about 0.05 to 100 mg (per day) for topical applications. Specific administration routes and dose levels (including the optimal dose) for any particular patient will be employed depending upon a variety of factors including the patient's conditions (general health, the severity of the particular disease or symptom undergoing therapy, the presence or absence of complications thereof, etc.), the age, sex, body weight, and the like.

EXAMPLES, ETC.

Described below are examples, including assay examples, synthetic examples and formulation examples, of the present invention which are provided only for illustrative purposes, and not to limit the scope of the present invention. All the examples were carried out or can be carried out, unless otherwise disclosed herein specifically, by standard techniques which are well known and conventional to those skilled in the art.

Assay Examples

Described below are examples of pharmacological assays for the efficacy and safety of the compounds (1) of the present invention wherein their protocols and results are provided.

Assay Example 1

PDE IV Inhibition

<Protocol>

The assays for PDE IV activity were conducted according to Nicholson et al. method (Br. J. Pharmacol., 97, 889 (1989)).

PDE IV isozymes as used herein were separated from U937 culture cells by using an anion exchange chromatography. Type IV PDE isozyme was admixed with ethylene glycol (EG) to adjust the final EG concentration to 30%, then stored at −20° C. and diluted when used. The enzymatic activity for PDE IV was measured using cAMP as a substrate.

[$^3$H]-cAMP (962 GBq/mmol; Amersham, 25 µl (100,000 cpm)) was added together with PDE IV isozyme (25 µl) to an incubation buffer solution with the composition given below to adjust the total volume to 250 µl. Each test compound was dissolved in DMSO to adjust the final concentration to 1% (2.5 µl/tube).

Incubation Buffer Solution (pH7.5):
    Tris-HCl (50 mM), magnesium chloride (6 mM), dithiothreitol (2.5 mM), 5-nucleotidase (4 µg/ml), bovine serum albumin (0.23 mg/ml), and cAMP (1 µM).

A mixture of the aforementioned test compound solution and the buffer solution was incubated at 30° C. for 20 minutes. The reaction was quenched by admixing with 1 ml of anion exchange resin slurry (AG1-X8, 200-400 meshes, chloride form; Bio-Rad) to absorb unreacted substrates. After the reaction stopped, the mixture was centrifuged at 800×g for 10 minutes, and the resulting supernatant was collected with vials in 250 µl aliquots. To each vial was added 5 ml of ACS-II (scintillator, Amersham). The radioactivity was measured with a liquid scintillator counter for [$^3$H]-adenosine and set as the PDE IV activity.

The % inhibition was calculated for test compounds, and IC$_{50}$ (the concentration of each test compound required for 50% inhibition) was obtained by Probit method. The results are shown in Table 1. Rolipram [(−)-4-[3-(cyclopentyloxy)-4-methoxyphenyl]-2-pyrrolidinone], already known as the PDE IV inhibitor in the prior art, was used for the reference compound in this assay.

TABLE 1

| Test Compounds | Inhibition of PDE IV (IC$_{50}$; µM) |
| --- | --- |
| Example No. 5 | 0.067 |
| Example No. 6 | 0.025 |
| Example No. 9 | 0.084 |
| Example No. 13 | 0.031 |
| Example No. 14 | 0.057 |
| Example No. 21 | 0.088 |
| Example No. 22 | 0.026 |
| Example No. 23 | 0.082 |
| Example No. 26 | 0.020 |
| Example No. 27 | 0.021 |
| Example No. 30 | 0.049 |
| Example No. 32 | 0.028 |
| Example No. 33 | 0.068 |
| Example No. 41 | 0.089 |
| Example No. 43 | 0.086 |
| Example No. 46 | 0.032 |
| Example No. 53 | 0.028 |
| Example No. 56 | 0.023 |
| Example No. 58 | 0.035 |
| Rolipram | 0.19 |

<Conclusion>

As seen in Table 1, it has been verified that the compounds of the present invention inhibit potently PDE IV.

Assay Example 2

Inhibition of Antigen-Induced Immediate Asthmatic Response (Anti-Asthmatic Action)

<Protocol>

(1) Active Sensitization of Guinea Pigs

Male Hartley outbred guinea pigs were sensitized by administering intraperitoneally physiological saline (0.5 ml) containing ovalbumin (1 mg, antigen) and 5×10$^9$ inactivated *Bordetella pertussis* dead cells (adjuvant). Eleven to thirteen days after the first sensitization, 0.05 ml of an ovalbumin solution (1 mg/ml) (ovalbumin is dissolved in physiological saline) was administered to the lateroabdominal region of each guinea pig intracutaneously. An establishment of sensitization was checked relying on cutaneous reaction. Only guinea pigs wherein significant reddening responses occurred 5 to 10 minutes later were employed in the next measurement test for airway resistance.

(2) Measurement for Airway Resistance in Actively Sensitized-Guinea Pigs

The guinea pigs (3 animals per group) actively sensitized in the above step (1) were employed to measure for their airway pressure according to Konzett-Rossler method (Arch. Exp. Path. Pharmakol., 195, 71 (1940)).

Thirteen days after the final sensitization, guinea pigs fasted overnight, and were on the next day anesthetized with a pentobarbital solution (30 mg/1.2 ml/kg, dissolved in physiological saline, intraperitoneal administration). After the guinea pigs were fixed in a supine position, their trachea was incised followed by insertion with one port of a 4-port cannula. Among the remaining 3 ports, 2 ports were connected to an artificial respirator (Model 683, Harvard). The animals were ventilated with 10 ml/kg of air per ventilation at a rate of 60 beats/min via the artificial respirator from the cannula. One port remainder was connected to a respiratory amplifier (AR-601G, Nihon Kohden, Japan) via an airflow resistance tube (TV-241T, Nihon Kohden, Japan) and a differential pressure transducer (TP-602T, Nihon Kohden, Japan) connected with a control box (RY-111S, Nihon Kohden, Japan). From a catheter inserted into a left carotid artery, blood pressures were monitored with a blood pressure measurement unit (AP641G, NEC Corp., Japan) via a blood pressure transducer (TP-300T, Nihon Kohden, Japan), and heart rates were recorded on a thermal recorder (WT-685G, Nihon Kohden, Japan), relying on blood pressure pulse waves after being led to a cardiograph unit (AT601G, Nihon Kohden, Japan).

After airway pressure became stable, an ovalbumin solution (1 mg/ml, dissolved in physiological saline) was administered at a dose of 1 ml/kg via a tube with which the right jugular vein of guinea pigs was cannulated. Each area under airway pressure-time curve (AUC) was obtained by measuring amplitudes of the airway pressure prior to the antigen-challenge, 1, 2, 3, 4, 5, 10, 15 and 20 minutes post-challenge, and each percent increase (%) in airway resistance was further calculated according to the following equation:

$$\text{Percent Increase (\%) in Airway Resistance} = \left( \frac{\text{AUC for 20 min after Antigen-Challenge}}{\text{Basal Respiratory Pressure}} - 1 \right) \times 100$$
$$\text{AUC for 20 min after Antigen-Challenge}$$

Each test compound was suspended in 0.5% CMC-Na solution and administered orally with an oral sound at a dose of 0.03 to 20 mg/2 ml/kg 60 minutes prior to the antigen-challenge. Control groups received only 0.5% CMC-Na solution in an equivalent amount. The pentobarbital-anesthetization and tracheal incision were conducted 30 minutes prior to the antigen-challenge.

Each percent reduction of increase in airway resistance (each test compound-administered group versus control group) was calculated according to the equation given below. ED$_{50}$ was obtained by Probit method. The results are shown in Table 2. Rolipram, SB207499 (cis-4-cyano-4-[3-(cyclopentyloxy)-4-methoxyphenyl]cyclohexane-1-carboxylic acid; disclosed in J. Med., Chem., 41, 821 (1998), etc.), and Roflumilast (3-(cyclopropylmethoxy)-N-(3,5-dichloro-4-pyridyl)-4-(difluoromethoxy)benzamide) were used for the reference compounds in this assay.

$$\text{Percent Reduction (\%) of Increase in Airway Resistance} = 100 - \left( \frac{\text{Percent Increase in Airway Resistance (Test Compound-Administered Group)}}{\text{Percent Increase in Airway Resistance (Control Group)}} \right) \times 100$$

TABLE 2

| Test Compounds | Inhibition of Asthmatic response ED$_{50}$: mg/kg orally |
| --- | --- |
| Example No. 9 | 0.16 |
| Example No. 33 | 0.33 |
| Roflumilast | 0.66 |
| Rolipram | 0.51 |
| SB207499 | >20 |

<Conclusion>

As seen in Table 2, it has been verified that the compounds of the present invention exert an excellent inhibitory action on antigen-induced immediate asthmatic responses.

Assay Example 3

Inhibition of TNF-α Production in Galactosamine- and Lipopolysaccharide (LPS)-Stimulation <Protocol>

A suspension of each test compound in 0.5% CMC-Na solution was administered orally to C3H/HeN mice at a dose of 0.10 to 10 mg/kg. One hour later, the animals received intravenously galactosamine at a dose of 800 mg/kg and LPS at a dose 5 μg/kg to raise the induction of TNF-α production. One hour later after the galactosamine- and LPS-administration, amounts of TNF-α in serum samples were measured by ELISA, and $ED_{50}$ was obtained. The results are shown in Table 3. Roflumilast and SB207499 were used for the reference compounds in this assay.

TABLE 3

| Test Compounds | Inhibition of TNF-α production $ED_{50}$: mg/kg orally |
|---|---|
| Example No. 9 | 0.22 |
| Example No. 33 | 0.10 |
| Roflumilast | 0.26 |
| SB207499 | 3.3 |

<Conclusion>

As seen in Table 3, it has been verified that the compounds (Example Nos. 9 and 33) have a better inhibitory action on TNF-α production.

Assay Example 4

Inhibition of Drug-Metabolizing Enzymes

<Protocol>

The inhibitory effect on CYP2D6 and CYP3A4 was determined using High Throughput Inhibitor Screening Kits: CYP2D6/AMMC and CYP3A4/BFC (both from BD Biosciences, NJ, USA). Briefly, each of NADPH regenerating systems, cofactors, and test compounds was dispensed into 96-well plates, followed by addition of each of fluorescent substrates, AMMC (CYP2D6) or BFC (CYP3A4). To each well were added CYP2D6-expressing system microsomes or CYP3A4-expressing system microsomes, and the plates were incubated at 37° C. for 30 minutes, and then read for fluorescent signals (CYP2D6: ex=390 nm, em=460 nm; CYP3A4: ex=409 nm, em=538 nm wherein excitation wavelength: ex and emission wavelength: em). Thus, each inhibitory efficacy on enzymes CYP2D6 and CYP3A4 was determined. The results are shown in Table 4. Roflumilast was used for the reference compound in this assay.

TABLE 4

| Test Compounds | Inhibition of Drug-Metabolizing Enzymes ($IC_{50}$; μM) | |
|---|---|---|
| | CYP2D6 | CYP3A4 |
| Example No. 9 | >10 | 8.5 |
| Example No. 33 | >10 | 6.2 |
| Roflumilast | 9.1 | 0.98 |

<Conclusion>

As seen in Table 4, it has been verified that the compounds (Example Nos. 9 and 33) are less inhibitory to drug-metabolizing enzymes (CYP2D6 and CYP3A4).

Assay Example 5

Inhibition of Lung Eosinophil Infiltration

<Protocol>

Hartley guinea-pigs were sensitized by inhaling twice 1% ovalbumin (OVA) in a physiological saline for 10 minutes with a nebulizer (Atom Medical Corporation, Japan) at an interval of 1 week. The animals were orally given a suspension of test compounds at a dose of 0.03 to 3 mg/2 mL/kg one week after the final sensitization. One hour later, the animals were exposed to antigens by inhalation of 2% OVA in a physiological saline for 5 minutes with a nebulizer. Thirty minutes before the antigen challenge, the animals were intraperitoneally pretreated with pyrilamine at a dose of 10 mg/kg to avoid fatality due to anaphylactic shock. Bronchoalveolar lavage fluid (BALF) samples were collected 24 hours after the exposure by inhalation of antigens, and eosinophils were counted.

TABLE 5

| Test Compounds | Inhibition of Lung Eosinophil Infiltration $ED_{50}$: mg/kg orally |
|---|---|
| Example No. 9 | <0.03 |
| Example No. 33 | 0.03 |
| Roflumilast | 0.36 |

<Conclusion>

It has been verified that the compounds of the present invention (Example Nos. 9 and 33) are more inhibitory on lung eosinophil infiltration than Roflumilast.

Assay Example 6

Inhibition of Lung Neutrophil Infiltration

<Protocol>

Hartley guinea-pigs were orally received a suspension of test compounds at a dose of 0.03 to 3 mg/2 mL/kg. One hour later, the animals were received 0.1 mg/mL lipopolylsaccharide (LPS) in a physiological saline via an inhalational route with a nebulizer for 30 minutes. Twenty-four hours after the LPS inhalation, BALF samples were collected, and neutrophils were counted.

TABLE 6

| Test Compounds | Inhibition of Lung Neutrophil Infiltration $ED_{50}$: mg/kg orally |
|---|---|
| Example No. 9 | 0.12 |
| Example No. 33 | 0.09 |
| Roflumilast | 0.98 |

<Conclusion>

It has been verified that the compounds of the present invention (Example Nos. 9 and 33) are more inhibitory on lung neutrophil infiltration than Roflumilast.

Assay Example 7

Toxicology Study (1-Week-administration to Mice)

<Protocol>

The Compound of the present invention (Example No. 9) was administered orally to ICR mice (5 animals per group) as a test compound. During one week, the mice were observed for the time course of their general health conditions and measured for their body weight. The test compound was suspended in 0.5% CMC-Na solution and given orally to the animal at a dose of 100 or 300 mg/10 ml/kg in a forced manner.

<Conclusion>

None of the animals were died in every dose group when the test compound was administered. No reduction of body weight gains was observed, either. Further, no abnormality was observed for other parameters.

Assay Example 8

Toxicology Study (2-Weeks-administration to Rats)

<Protocol>

Each compound of the present invention (Example Nos. 9 and 33) was administered orally to rats (6 animals per group) as a test compound. During 2 weeks, the rats were observed for the time course of their general health conditions and measured for their body weight. The test compound was suspended in 0.5% CMC-Na solution and given orally to the animal at a dose of 1, 5, or 25 mg/5 ml/kg in a forced manner.

<Conclusion>

None of the animals were died in every dose group when the test compounds were administered. No significant reduction of body weight gains was observed, either. Further, no clear abnormality was observed for other parameters.

Assay Example 9

Emetic Action on Dogs

<Protocol>

Beagle dogs received a suspension of each test compound in 0.5% CMC-Na solution orally at a dose of 1 mg/2 mL/kg. The animals were observed for occurrence of emesis after the test compound administration.

<Conclusion>

When the instant compounds (Example Nos. 9 & 33 Compounds) were orally administered to the beagle dogs, there was no observation for emetic actions at the dose of 1 mg/kg.

In contrast, it was found that 2 animals among 3 were afflicted with emetic reactions for the test reference compound, Roflumilast, even at the dose of 1 mg/kg.

In conclusion, it has been verified that the instant compounds, Example Nos. 9 & 33 Compounds, are less emetic than Roflumilast.

Synthetic Examples

Described below are Synthetic Examples 1 to 28 for the compounds of the formula (2).

Synthetic Example 1

4-hydroxy-3-[1-oxo-3-(pyridin-4-yl)propyl]-1-phenyl-1,8-naphthyridin-2 (1H)-one (1) A solution of ethyl 3-(pyridin-4-yl)propionate (17.14 g, 96 mmol; synthesized according to WO, A, 01/42244) in aqueous sodium hydroxide (2N, 100 ml) was heated under reflux for 1 hour, cooled, then adjusted pH 4 to 5 with conc. sulfuric acid, filtered to give precipitates which were washed with water, and then with hexane, and dried to afford 3-(pyridin-4-yl)propionic acid (10.15 g, 70%) as crystals.

$^1$H NMR(DMSO-$d_6$) δ:2.59 (2H, t, J=7.6 Hz), 2.83 (2H, t, J=7.6 Hz), 7.25-7.27 (2H, app-d, J=5.9 Hz), 8.44-8.46 (2H, app-d, J=5.9 Hz), 12.21 (1H, br)

(2) A mixture of 4-hydroxy-1-phenyl-1,8-naphthyridin-2 (1H)-one (2.0 g, 8.4 mmol; synthesized according to JP, A, 61-246183 (1986)), 3-(pyridin-4-yl)propionic acid (19.03 g, 126 mmol, 15 eq.) and polyphosphoric acid (about 100 ml) was heated overnight at 150° C. while stirring. The mixture was poured into water with stirring to form a solution while it was occasionally cooled. The operation including 3 times washing of the aqueous layer with chloroform, then addition of saturated aqueous sodium hydrogen carbonate followed by occasional extraction with chloroform was repeated until the aqueous layer was made pH3 to 3.5. The organic layers which were collected during neutralizing were pooled, dried over anhydrous magnesium sulfate, and then evaporated to give a residue which was purified by flash column chromatography to afford 4-hydroxy-3-[1-oxo-3-(pyridin-4-yl)propyl]-1-phenyl-1,8-naphthyridin-2 (1H)-one (1.59 g, 51%) as crystals.

mp 206-208° C. $^1$H NMR(CDCl$_3$)δ:3.06 (2H, t, J=7.6 Hz), 3.67 (2H, t, J=7.6 Hz), 7.20-7.27 (3H, m), 7.23-7.25 (2H, app-d, J=4.3 Hz), 7.47-7.62 (3H, m), 8.47-8.49 (2H, app-d, J=4.9 Hz), 8.52-8.58 (2H, m)

Synthetic Example 2

4-hydroxy-3-[1-oxo-3-(pyridin-3-yl)propyl]-1-phenyl-1,8-naphthyridin-2 (1H)-one (1) A mixture of 3-(pyridin-3-yl)propenoic acid (10.0 g, 67 mmol), 10% palladium-activated carbon (1 g), methanol (100 mL) and ethanol (100 mL) was stirred overnight under hydrogen atmosphere. The resultant reaction mixture was filtered, evaporated, and dried to give 3-(pyridin-3-yl)propionic acid (10.2 g, quantitative).

$^1$H NMR(DMSO-$d_6$) δ:2.52 (2H, m), 2.81 (2H, t, J=7.6 Hz), 7.27-7.31 (1H, app-dd, J=4.6 Hz, 7.9 Hz), 7.63-7.67 (1H, app-dt, J=7.9H, 1.7 Hz), 8.38-8.40 (1H, app-dd, J=1.7 Hz, 4.6 Hz), 8.44-8.45 (1H, app-d, J=1.7 Hz)

(2) The procedure of Synthetic Example 1 was repeated using 4-hydroxy-1-phenyl-1,8-naphthyridin-2 (1H)-one (402 mg, 1.7 mmol; synthesized according to JP, A, 61-246183

(1986)), 3-(pyridin-3-yl)propionic acid (3.81 g, 25.2 mmol, 15 eq.) and polyphosphoric acid (10 ml) to afford 4-hydroxy-3-[1-oxo-3-(pyridin-3-yl)propyl]-1-phenyl-1,8-naphthyridin-2 (1H)-one (283 mg, 45%).

mp 219-220° C. $^1$H NMR(CDCl$_3$) δ:3.09 (2H, t, J=7.3 Hz), 3.67 (2H, t, J=7.3 Hz), 7.20-7.37 (4H, m), 7.50-7.61 (3H, m), 7.75-7.78 (1H, app-d, J=7.6 Hz), 8.46-8.58 (4H, m)

Synthetic Example 3

4-hydroxy-3-[1-oxo-2-(pyridin-3-yl)ethyl]-1-phenyl-1,8-naphthyridin-2 (1H)-one (1) To a suspension of 2-(pyridin-3-yl)acetic acid-hydrochloride (13.2 g, 75.6 mmol) in ethanol (100 mL) was added a solution (150 mL) of 0.5 mol potassium hydroxide/ethanol, and the mixture was stirred well, then filtered to remove potassium chloride, concentrated, and dried to give 2-(pyridin-3-yl)acetic acid (10.6 g, quantitative).

(2) The procedure of Synthetic Example 1 was repeated using 4-hydroxy-1-phenyl-1,8-naphthyridin-2 (1H)-one (712 mg, 3.0 mmol; synthesized according to JP, A, 61-246183 (1986)), 2-(pyridin-3-yl)acetic acid (8.23 g, 60 mmol, 20 eq.) and polyphosphoric acid (1 ml) to afford 4-hydroxy-3-[1-oxo-2-(pyridin-3-yl)ethyl]-1-phenyl-1,8-naphthyridin-2 (1H)-one (203 mg, 19%).

mp 186-188° C. $^1$H NMR(CDCl$_3$) δ:4.67 (2H, s), 7.21-7.29 (3H, m), 7.53-7.74 (5H, m), 8.52-8.55 (2H, app-d, J=7.9 Hz), 8.57-8.59 (2H, app-dd, J=1.7 Hz, 4.6 Hz)

Synthetic Example 4

4-hydroxy-1-(3-nitrophenyl)-3-[1-oxo-3-(pyridin-4-yl)propyl]-1,8-naphthyridin-2 (1H)-one (1) To methyl 2-(3-nitrophenylamino)nicotinate (5.00 g, 18.3 mmol; synthesized according to WO, A, 01/42244) was added 1,2-dichloroethane (90 ml ), and the mixture was heated at 80° C. to form a solution. To the resultant solution was added trichloromethyl chloroformate (also called: diphosgene, 6.7 ml, 54.9 mmol) gradually dropwise over about 30 minutes. Three hours later, the mixture was admixed with activated carbon (150 mg), heated under reflux for 30 minutes, filtered, then evaporated, and dried under reduced pressure to give a mixture (5.32 g, quantitative) containing 1-(3-nitrophenyl)-2H-pyrido[2,3-d][1,3]oxazin-2,4(1H)-dione as crystals.

mp 209-212° C.(dec.) $^1$H NMR(CDCl$_3$) δ: 7.33-7.38 (1H, app-dd, J=4.9 Hz, 7.9 Hz), 7.70-7.74 (1H, app-td, J=1.7 Hz, 7.9 Hz), 7.75-7.81 (1H, app-dt, J=0.7 Hz, 7.9 Hz), 8.27-8.28 (1H, app-t, J=2.0 Hz), 8.39-8.43 (1H, app-ddd, J=1.7 Hz, 2.0 Hz, 7.9 Hz), 8.51-8.54 (1H, app-dd, J=2.0 Hz, 7.6 Hz), 8.50-8.58 (1H, app-dd, J=2.0 Hz, 4.9 Hz)

(2) To a solution of diethyl malonate (2.99 g, 18.7 mmol) in dimethylacetamide (28 ml ) was added sodium hydride (about 60%, 933 mg, 23.3 mmol) with ice-cooling, and the mixture was stirred to form a solution until the production of hydrogen was completed. After the resultant solution was added to a mixture (5.32 g) containing1-(3-nitrophenyl)-2H-pyrido[2,3-d][1,3]oxazin-2,4(1H)-dione with ice-cooling, the mixture was stirred for 3 hours at 150° C., cooled to room temperature, then treated with ethyl acetate, and allowed to stand. The resulting precipitate was filtered off, and washed with ethyl acetate. The residue obtained after filtration was dissolved in water, acidified to pH1 with hydrochloric acid to form precipitates which were filtered off, washed with water, and dried to give 3-ethoxycarbonyl-4-hydroxy-1-(3-nitrophenyl)-1,8-naphthyridin-2(1H)-one (4.42 g, yield for 2 steps from (1): 66%) as crystals.

mp 309-312° C.(dec.) $^1$H NMR(CDCl$_3$) δ: 1.44 (3H, t, J=7.3 Hz), 4.49 (2H, q, J=7.3 Hz), 7.24-7.29 (1H, m), 7.60-7.64 (1H, app-ddd, J=1.0 Hz, 2.0 Hz, 7.9 Hz), 7.69-7.75 (1H, app-t, J=7.9 Hz), 8.16-8.18 (1H, app-t, J=2.0 Hz), 8.33-8.37 (1H, app-ddd, J=1.0 Hz, 2.0 Hz, 7.9 Hz), 8.51 (1H, s), 8.52-8.54 (1H, app-dd, J=2.0 Hz, 4.0 Hz), 14.55 (1H, s)

(3) To 3-ethoxycarbonyl-4-hydroxy-1-(3-nitrophenyl)-1,8-naphthyridin-2 (1H)-one (4.42 g, 12.4 mmol) was added an aqueous solution (18 ml) of potassium hydroxide (2.44 g, 43.4 mmol), and the mixture was heated under reflux overnight, treated with activated carbon (150 mg), refluxed for 10 minutes, and filtered off. The resultant solution was acidified to pH1 with hydrochloric acid, filtered off to give precipitates which were washed with water and dried to afford 4-hydroxy-1-(3-nitrophenyl)-1,8-naphthyridin-2 (1H)-one (3.52 g, quantitative) as crystals.

mp 293-295° C.(dec.) $^1$H NMR(DMSO-d$_6$) δ: 5.97 (1H, s), 7.28-7.33 (1H, app-dd, J=4.6 Hz, 7.9 Hz), 7.78-7.81 (2H, m), 8.20-8.33 (3H, m), 8.40-8.43 (1H, app-dd, J=2.0 Hz, 4.9 Hz), 12.01 (1H, brs)

(4) The procedure of Synthetic Example 1 was repeated using a mixture of 4-hydroxy-1-(3-nitrophenyl)-1,8-naphthyridin-2 (1H)-one (2.5 g, 8.83 mmol), 3-(pyridin-4-yl)propionic acid (19.87 g, 131 mmol, 15 eq.; prepared in Synthetic Example 1-(1)) and polyphosphoric acid (about 100 ml) to obtain 4-hydroxy-1-(3-nitrophenyl)-3-[1-oxo-3-(pyridin-4-yl)propyl]-1,8-naphthyridin-2 (1H)-one (1.98 g, 54%).

mp 174-177° C. $^1$H NMR(CDCl$_3$) δ:3.05 (2H, t, J=7.3 Hz), 3.63 (2H, t, J=7.3 Hz), 7.20-7.22 (2H, app-d, J=5.9 Hz), 7.27-7.31 (1H, app-dd, J=4.6 Hz, 7.9 Hz), 7.60-7.64 (1H, app-ddd, J=1.0 Hz, 1.6 Hz, 7.9 Hz), 7.73-7.78 (1H, app-t, J=7.9 Hz), 8.16-8.18 (1H, app-t, J=2.0 Hz), 8.35-8.39 (1H, app-ddd, J=1.0 Hz, 2.3 Hz, 8.2 Hz), 8.47-8.49 (2H, app-d, J=5.9 Hz), 8.52-8.54 (1H, app-dd, J=2.0 Hz, 4.6 Hz), 8.55-8.59 (1H, app-dd, J=2.0 Hz, 7.9 Hz)

Synthetic Example 5

4-hydroxy-3-(1-oxo-2-phenylethyl)-1-phenyl-1,8-naphthyridin-2 (1H)-one (1) A mixture of 4-hydroxy-1-phenyl-1,8-naphthyridin-2 (1H)-one (1.19 g, 5.0 mmol; synthesized according to JP, A, 61-246183 (1986)) and sodium hydride (about 60%, 200 mg, 5.0 mmol) was added DMF (10 ml), and the resultant mixture was stirred to form a solution until the production of hydrogen was completed. Next, after phenylacetyl chloride (0.8 ml, 6 mmol) was added, the mixture was stirred for 1 hour at 50° C., treated with saturated aqueous sodium hydrogen carbonate, and filtered off to give precipitates which were washed with water and dried to afford 1-phenyl-4-phenylacetoxy-1,8-naphthyridin-2 (1H)-one (1.34 g, 75%).

mp 179-180° C./DMF-H$_2$O $^1$H NMR(CDCl$_3$) δ:4.01 (2H, s), 6.77 (1H, s), 7.06 (1H, dd, J=4.9 Hz, 7.9 Hz), 7.24-7.28 (2H, m), 7.38-7.60 (8H, m), 7.63 (1H, dd, J=2.0 Hz, 7.9 Hz), 8.44 (1H, dd, J=2.0 Hz, 4.9 Hz)

(2) To a mixture of 1-phenyl-4-phenylacetoxy-1,8-naphthyridin-2 (1H)-one (1.34 g, 3.7 mmol), triethylamine (379 mg, 3.7 mmol), potassium cyanide (491 mg, 7.5 mmol), and 18-crown-6 (197 mg) was added dry toluene (35 ml), and the mixture was stirred at room temperature overnight, admixed with saturated aqueous sodium hydrogen carbonate and dichloromethane. The organic layer was washed with saturated aqueous sodium hydrogen carbonate, and successively with saturated aqueous sodium chloride. The organic layer was collected, dried over anhydrous magnesium sulfate, and evaporated. The resulting residue was purified by flash column chromatography to afford 4-hydroxy-3-(1-oxo-2-phenylethyl)-1-phenyl-1,8-naphthyridin-2 (1H)-one (583 mg, 44%) as crystals.

mp 169-170° C. $^1$H NMR(CDCl$_3$) δ:4.64 (2H, s), 7.21 (1H, dd, J=4.6 Hz, 7.9 Hz), 7.25-7.38 (7H, m), 7.49-7.64 (3H, m), 8.52 (1H, dd, J=2.0 Hz, 7.9 Hz), 8.56 (1H, dd, J=2.0 Hz, 4.6 Hz)

Synthetic Example 6

4-hydroxy-3-(1-oxo-3-phenylpropyl)-1-phenyl-1,8-naphthyridin-2 (1H)-one

The procedure of Synthetic Example 5 was repeated using phenylpropionyl chloride in place of phenylacetyl chloride to obtain 4-hydroxy-3-(1-oxo-3-phenylpropyl)-1-phenyl-1,8-naphthytidin-2 (1H)-one, mp 233-234° C. (yield for 2 steps, 51%).

$^1$H NMR(CDCl$_3$) δ:3.03 (2H, t, J=7.3 Hz), 3.64 (2H, t, J=7.3 Hz), 7.12-7.26 (8H, m), 7.46-7.60 (3H, m), 8.53 (1H, dd, J=2.0 Hz, 7.9 Hz), 8.56 (1H, dd, J=2.0 Hz, 4.9 Hz)

Synthetic Example 7

4-hydroxy-3-[1-oxo-3-(4-nitrophenyl)propyl]-1-phenyl-1,8-naphthyridin-2 (1H)-one The procedure of Synthetic Example 5 was repeated using 4-nitrophenylpropionyl chloride in place of phenylacetyl chloride to obtain 4-hydroxy-3-[1-oxo-3-(4-nitrophenyl)propyl]-1-phenyl-1,8-naphthyridin-2 (1H)-one, mp 215-217° C. (yield for 2 steps, 52%)).

$^1$H NMR(CDCl$_3$) δ:3.14 (2H, t, J=7.3 Hz), 3.68 (2H, t, J=7.3 Hz), 7.20-7.25 (3H, m), 7.39-7.42 (2H, app-d, J=8.2 Hz), 7.47-7.62 (3H, m), 8.10-8.13 (2H, app-d, J=8.6 Hz), 8.53 (1H, dd, J=1.7 Hz, 7.9 Hz), 8.57 (1H, dd, J=1.6 Hz, 4.6 Hz)

Synthetic Example 8

4-hydroxy-3-[1-oxo-3-(4-cyanophenyl)propyl]-1-phenyl-1,8-naphthyridin-2 (1H)-one The procedure of Synthetic Example 5 was repeated using 4-cyanophenylpropionyl chloride in place of phenylacetyl chloride to obtain 4-hydroxy-3-[1-oxo-3-(4-cyanophenyl)propyl]-1-phenyl-1,8-naphthyridin-2 (1H)-one, mp 248-249° C. (yield for 2 steps, 58%).

$^1$H NMR(CDCl$_3$) δ:3.09 (2H, t, J=7.3 Hz), 3.65 (2H, t, J=7.3 Hz), 7.20-7.26 (3H, m), 7.34-7.37 (2H, app-d, J=8.2 Hz), 7.46-7.62 (3H, m), 7.53-7.56 (2H, app-d, J=7.9 Hz), 8.53 (1H, dd, J=1.7 Hz, 7.9 Hz), 8.57 (1H, dd, J=1.7 Hz, 4.6 Hz)

Synthetic Example 9

4-hydroxy-3-[1-oxo-3-(3-nitrophenyl)propyl]-1-phenyl-1,8-naphthyridin-2 (1H)-one The procedure of Synthetic Example 5 was repeated using 3-nitrophenylpropionyl chloride in place of phenylacetyl chloride to obtain 4-hydroxy-3-[1-oxo-3-(3-nitrophenyl)propyl]-1-phenyl-1,8-naphthyridin-2 (1H)-one, mp 164-166° C. (yield for 2 steps, 27%).

$^1$H NMR(CDCl$_3$) δ:3.14 (2H, t, J=7.3 Hz), 3.68 (2H, t, J=7.3 Hz), 7.20-7.25 (3H, m), 7.39-7.45 (1H, app-t, J=7.9 Hz), 7.47-7.61 (4H, m), 8.01-8.06 (1H, m), 8.11-8.13 (1H, m), 8.52-8.55 (1H, app-dd, J=2.0 Hz, 7.9 Hz), 8.56-8.58 (1H, app-dd, 2.0 Hz, 5.0 Hz)

Synthetic Example 10

4-hydroxy-3-[1-oxo-3-(2-nitrophenyl)propyl]-1-phenyl-1,8-naphthyridin-2 (1H)-one The procedure of Synthetic Example 5 was repeated using 2-nitrophenylpropionyl chloride in place of phenylacetyl chloride to obtain 4-hydroxy-3-[1-oxo-3-(2-nitrophenyl)propyl]-1-phenyl-1,8-naphthyridin-2 (1H)-one, mp 238-240° C. (yield for 2 steps, 58%).

$^1$H NMR(CDCl$_3$) δ:3.30 (2H, t, J=7.9 Hz), 3.70 (2H, t, J=7.9 Hz), 7.20-7.25 (3H, m), 7.31-7.40 (2H, m), 7.46-7.59 (4H, m), 7.91-7.93 (1H, app-d, J=7.9 Hz), 8.53-8.58 (2H, m)

Synthetic Example 11

4-hydroxy-3-[1-oxo-3-(2-cyanophenyl)propyl]-1-phenyl-1,8-naphthyridin-2 (1H)-one The procedure of Synthetic Example 5 was repeated using 2-cyanophenylpropionyl chloride in place of phenylacetyl chloride to obtain 4-hydroxy-3-[1-oxo-3-(2-cyanophenyl)propyl]-1-phenyl-1,8-naphthyridin-2 (1H)-one, mp 226-227° C. (yield for 2 steps, 52%).

$^1$H NMR(CDCl$_3$) δ:3.26 (2H, t, J=7.3 Hz), 3.67 (2H, t, J=7.3 Hz), 7.20-7.37 (5H, m), 7.44-7.61 (5H, m), 8.53-8.58 (2H, m)

Synthetic Example 12

4-hydroxy-3-[1-oxo-3-(3-cyanophenyl)propyl]-1-phenyl-1,8-naphthyridin-2 (1H)-one The procedure of Synthetic Example 5 was repeated using 3-cyanophenylpropionyl chloride in place of phenylacetyl chloride to obtain 4-hydroxy-3-[1-oxo-3-(3-cyanophenyl)propyl]-1-phenyl-1,8-naphthyridin-2 (1H)-one, mp 219-220° C. (yield for 2 steps, 30%).

$^1$H NMR(CDCl$_3$) δ:3.06 (2H, t, J=7.3 Hz), 3.64 (2H, t, J=7.3 Hz), 7.20-7.25 (3H, m), 7.32-7.38 (1H, t, J=7.6 Hz), 7.45-7.62 (6H, m), 8.52-8.55 (1H, dd, J=2.0 Hz, 7.9 Hz), 8.56-8.58 (1H, dd, J=2.0 Hz, 4.6 Hz)

Synthetic Example 13

4-hydroxy-3-[1-oxo-3-(4-methylphenyl)propyl]-1-phenyl-1,8-naphthyridin-2 (1H)-one The procedure of Synthetic Example 5 was repeated using 4-methylphenylpropionyl chloride in place of phenylacetyl chloride to obtain 4-hydroxy-3-[1-oxo-3-(4-methylphenyl)propyl]-1-phenyl-1,8-naphthyridin-2 (1H)-one, mp 232-234° C. (yield for steps, 22%)).

$^1$H NMR(CDCl$_3$) δ:2.29 (3H, s), 2.99 (2H, t, J=7.6 Hz), 3.62 (2H, t, J=7.6 Hz), 7.03-7.06 (2H, app-d, J=7.9 Hz), 7.11-7.14 (2H, app-d, J=7.9 Hz), 7.18-7.26 (3H, m), 7.46-7.60 (3H, m), 8.50-8.56 (2H, m)

Synthetic Example 14

4-hydroxy-3-[1-oxo-2-(3-methoxyphenyl)ethyl]-1-phenyl-1,8-naphthyridin-2 (1H)-one To a solution of 4-hydroxy-1-phenyl-1,8-naphthyridin-2 (1H)-one (504 mg, 2.12 mmol; synthesized according to JP, A, 61-246183 (1986)) in DMF (20 ml) was added sodium hydride (60%, 167 mg, 2.0 eq.) while ice-cooling, and the mixture was stirred to form a solution until the production of hydrogen was completed (for about 30 minutes), Next, after 3-methoxyphenylacetyl chloride (410 mg, 2.22 mmol, 1.05 eq.) was added, the mixture was stirred at room temperature, admixed with water, acidified with hydrochloric acid, and then filtered off to give precipitates which were washed with water, dried, and then evaporated. The resulting residue was purified by flash column chromatography to afford 4-hydroxy-3-[1-oxo-2-(3-methoxyphenyl)ethyl]-1-phenyl-1,8-naphthyridin-2 (1H)-one (423 mg, 52%).

mp 173-174° C. $^1$H NMR(CDCl$_3$) δ:3.79 (3H, s), 4.62 (2H, s), 6.81-6.90 (3H, m), 7.18-7.29 (4H, m), 7.49-7.64 (3H, m), 8.50-8.54 (1H, app-dd, J=2.0 Hz, 7.9 Hz), 8.55-8.58 (1H, app-dd, J=2.0 Hz, 4.6 Hz)

Synthetic Example 15

4-hydroxy-3-[1-oxo-2-(4-methoxyphenyl)ethyl]-1-phenyl-1,8-naphthyridin-2 (1H)-one The procedure of Synthetic Example 14 was repeated using 4-methoxyphenylacetyl chloride in place of 3-methoxyphenylacetyl chloride to obtain 4-hydroxy-3-[1-oxo-2-(4-methoxyphenyl)ethyl]-1-phenyl-1,8-naphthyridin-2 (1H)-one (55%), mp 190-191.5° C.

$^1$H NMR(CDCl$_3$) δ:3.80 (3H, s), 4.58 (2H, s), 6.80-6.90 (2H, m), 7.18-7.30 (5H, m), 7.49-7.63 (3H, m), 8.49-8.53 (1H, app-dd, J=1.9 Hz, 8.1 Hz), 8.55-8.57 (1H, app-dd, J=1.9 Hz, 4.9 Hz)

Synthetic Example 16

4-hydroxy-3-[1-oxo-2-(2-methoxyphenyl)ethyl]-1-phenyl-1,8-naphthyridin-2 (1H)-one The procedure of Synthetic Example 14 was repeated using 2-methoxyphenylacetyl chloride in place of 3-methoxyphenylacetyl chloride to obtain 4-hydroxy-3-[1-oxo-2-(2-methoxyphenyl)ethyl]-1-phenyl-1,8-naphthyridin-2 (1H)-one (50%), mp 203-205° C.

$^1$H NMR(CDCl$_3$) δ:3.78 (3H, s), 4.61 (2H, s), 6.90-6.98 (2H, m), 7.12-7.15 (1H, m), 7.19-7.23 (1H, app-dd, J=4.9 Hz, 7.6 Hz), 7.27-7.33 (3H, m), 7.49-7.64 (3H, m), 8.51-8.54 (1H, app-dd, J=1.9 Hz, 7.8 Hz), 8.56-8.58 (1H, app-dd, J=1.9 Hz, 4.9 Hz)

Synthetic Example 17

4-hydroxy-3-[1-oxo-2-(2-thienyl)ethyl]-1-phenyl-1,8-naphthyridin-2 (1H)-one

The procedure of Synthetic Example 14 was repeated using 2-thienylacetyl chloride in place of 3-methoxyphenylacetyl chloride to obtain 4-hydroxy-3-[1-oxo-2-(2-thienyl)ethyl]-1-phenyl-1,8-naphthyridin-2 (1H)-one (26%), mp 197-199° C.

$^1$H NMR(CDCl$_3$) δ:4.86 (2H, s), 6.98-7.01 (2H, m), 7.19-7.30 (4H, m), 7.50-7.64 (3H, m), 8.51-8.54 (1H, app-dd, J=2.0 Hz, 7.9 Hz), 8.56-8.58 (1H, app-dd, J=2.0 Hz, 4.6 Hz)

Synthetic Example 18

4-hydroxy-3-[1-oxo-2-(4-nitrophenyl)ethyl]-1-phenyl-1,8-naphthyridin-2 (1H)-one

The procedure of Synthetic Example 14 was repeated using 4-nitrophenylacetyl chloride in place of 3-methoxyphenylacetyl chloride to obtain 4-hydroxy-3-[1-oxo-2-(4-nitrophenyl)ethyl]-1-phenyl-1,8-naphthyridin-2 (1H)-one (20%), mp 223-227° C.

$^1$H NMR(CDCl$_3$) δ:4.74 (2H, s), 7.21-7.26 (1H, dd, J=4.6 Hz, 7.9 Hz), 7.26-7.29 (2H, m), 7.44-7.49 (2H, app-d, J=8.6 Hz), 7.49-7.65 (3H, m), 8.17-8.22 (2H, app-d, J=8.9 Hz), 8.52-8.55 (1H, dd, J=2.0 Hz, 7.9 Hz), 8.57-8.60 (1H, dd, J=2.0 Hz, 4.6 Hz)

Synthetic Example 19

4-hydroxy-3-[1-oxo-2-(3-nitrophenyl)ethyl]-1-phenyl-1,8-naphthyridin-2 (1H)-one

The procedure of Synthetic Example 14 was repeated using 3-nitrophenylacetyl chloride in place of 3-methoxyphenylacetyl chloride to obtain 4-hydroxy-3-[1-oxo-2-(3-nitrophenyl)ethyl]-1-phenyl-1,8-naphthyridin-2 (1H)-one (37%), mp 157-161° C.

$^1$H NMR(CDCl$_3$) δ:4.75 (2H, s), 7.21-7.26 (1H, dd, J=4.6 Hz, 7.9 Hz), 7.26-7.40 (2H, m), 7.48-7.67 (5H, m), 8.13-8.17 (2H, m), 8.52-8.55 (1H, dd, J=1.7 Hz, 7.9 Hz), 8.58-8.60 (1H, dd, J=1.7 Hz, 4.6 Hz)

Synthetic Example 20

4-hydroxy-3-[1-oxo-2-(2-nitrophenyl)ethyl]-1-phenyl-1,8-naphthyridin-2 (1H)-one

The procedure of Synthetic Example 14 was repeated using 2-nitrophenylacetyl chloride in place of 3-methoxyphenylacetyl chloride to obtain 4-hydroxy-3-[1-oxo-2-(2-nitrophenyl)ethyl]-1-phenyl-1,8-naphthyridin-2 (1H)-one (41%), mp 194-195° C.

$^1$H NMR(CDCl$_3$) δ:5.02 (2H, s), 7.21-7.25 (1H, dd, J=4.6 Hz, 7.9 Hz), 7.30-7.34 (3H, m), 7.47-7.66 (5H, m), 8.16-8.20 (1H, dd, J=1.3 Hz, 8.2 Hz), 8.51-8.54 (1H, dd, J=2.0 Hz, 7.9 Hz), 8.58-8.60 (1H, dd, J=2.0 Hz, 4.6 Hz)

Synthetic Example 21

4-hydroxy-3-[1-oxo-2-(2,5-dimethoxyphenyl)ethyl]-1-phenyl-1,8-naphthyridin-2 (1H)-one The procedure of Synthetic Example 14 was repeated using 2,5-dimethoxyphenylacetyl chloride in place of 3-methoxyphenylacetyl chloride to obtain 4-hydroxy-3-[1-oxo-2-(2,5-dimethoxyphenyl)ethyl]-1-phenyl-1,8-naphthyridin-2 (1H)-one (56%), mp 159-161° C.

$^1$H NMR(CDCl$_3$) δ:3.74 (3H, s), 3.77 (3H, s), 4.58 (2H, s), 6.71-6.84 (3H, m), 7.19-7.24 (1H, app-dd, J=4.6 Hz, 7.9 Hz), 7.27-7.33 (2H, m), 7.49-7.64 (3H, m), 8.51-8.54 (1H, app-dd, J=2.0 Hz, 7.9 Hz), 8.56-8.59 (1H, app-dd, J=2.0 Hz, 4.6 Hz)

Synthetic Example 22

4-hydroxy-3-[1-oxo-2-(3,4-dimethoxyphenyl)ethyl]-1-phenyl-1,8-naphthyridin-2 (1H)-one

The procedure of Synthetic Example 14 was repeated using 3,4-dimethoxyphenylacetyl chloride in place of 3-methoxyphenylacetyl chloride to obtain 4-hydroxy-3-[1-oxo-2-(3,4-dimethoxyphenyl)ethyl]-1-phenyl-1,8-naphthyridin-2 (1H)-one (52%), mp 161-163° C.

$^1$H NMR(CDCl$_3$) δ:3.86 (3H, s), 3.87 (3H, s), 4.58 (2H, s), 6.85 (3H, app-s), 7.19-7.23 (1H, app-dd, J=4.6 Hz, 7.6 Hz), 7.25-7.29 (2H, m), 7.50-7.65 (3H, m), 8.50-8.57 (2H, m)

Synthetic Example 23

4-hydroxy-3-[1-oxo-2-(3,5-dimethoxyphenyl)ethyl]-1-phenyl-1,8-naphthyridin-2 (1H)-one

The procedure of Synthetic Example 14 was repeated using 3,5-dimethoxyphenylacetyl chloride in place of 3-methoxyphenylacetyl chloride to obtain 4-hydroxy-3-[1-oxo-2-(3,5-dimethoxyphenyl)ethyl]-1-phenyl-1,8-naphthyridin-2 (1H)-one (35%), mp 169.5-171° C.

$^1$H NMR(CDCl$_3$) δ:3.77 (6H, s), 4.58 (2H, s), 6.38-6.40 (1H, app-t, J=2.3 Hz), 6.45-6.46 (2H, app-d, J=2.3 Hz), 7.19-7.24 (1H, app-dd, J=4.6 Hz, 7.9 Hz), 7.25-7.30 (3H, m), 7.52-7.63 (3H, m), 8.50-8.54 (1H, app-dd, J=2.0 Hz, 7.9 Hz), 8.55-8.58 (1H, app-dd, J=2.0 Hz, 4.6 Hz)

Synthetic Example 24

4-hydroxy-3-[1-oxo-2-(2,4-dimethoxyphenyl)ethyl]-1-phenyl-1,8-naphthyridin-2 (1H)-one

The procedure of Synthetic Example 14 was repeated using 2,4-dimethoxyphenylacetyl chloride in place of 3-methoxyphenylacetyl chloride to obtain 4-hydroxy-3-[1-oxo-2-(2,4-dimethoxyphenyl)ethyl]-1-phenyl-1,8-naphthyridin-2 (1H)-one (19%), mp 200-202° C.

$^1$H NMR(CDCl$_3$) δ:3.76 (3H, s), 3.82 (3H, s), 4.54 (2H, s), 6.46-6.50 (2H, m), 7.01-7.04 (1H, app-d, J=7.2 Hz), 7.18-7.23 (1H, app-dd, J=4.6 Hz, 7.2 Hz), 7.27-7.33 (2H, m), 7.49-7.63 (3H, m), 8.50-8.54 (1H, app-dd, J=2.0 Hz, 7.9 Hz), 8.55-8.58 (1H, app-dd, J=2.0 Hz, 4.6 Hz)

Synthetic Example 25

4-hydroxy-3-[1-oxo-2-(4-cyanophenyl)ethyl]-1-phenyl-1,8-naphthyridin-2 (1H)-one

The procedure of Synthetic Example 14 was repeated using 4-cyanophenylacetyl chloride in place of 3-methoxyphenylacetyl chloride to obtain 4-hydroxy-3-[1-oxo-2-(4-cyanophenyl)ethyl]-1-phenyl-1,8-naphthyridin-2 (1H)-one (18%), mp 227-230° C.

$^1$H NMR(CDCl$_3$) δ:4.69 (2H, s), 7.21-7.25 (1H, dd, J=4.6 Hz, 7.9 Hz), 7.25-7.29 (2H, m), 7.39-7.42 (2H, app-d, J=8.2 Hz), 7.50-7.68 (3H, m), 7.61-7.64 (2H, app-d, J=8.2 Hz), 8.51-8.55 (1H, dd, J=2.0 Hz, 7.9 Hz), 8.57-8.59 (1H, dd, J=1.6 Hz, 4.6 Hz)

Synthetic Example 26

4-hydroxy-3-[1-oxo-2-(4-ethoxycarbonylmethylphenyl)ethyl]-1-phenyl-1,8-naphthyridin-2 (1H)-one

The procedure of Synthetic Example 14 was repeated using 4-ethoxycarbonylmethylphenylacetyl chloride in place of 3-methoxyphenylacetyl chloride to obtain 4-hydroxy-3-[1-oxo-2-(4-ethoxycarbonylmethylphenyl)ethyl]-1-phenyl-1,8-naphthyridin-2 (1H)-one (22%), mp 156-158° C.

$^1$H NMR(CDCl$_3$) δ:1.25 (3H, t, J=7.3 Hz), 3.60 (2H, s), 4.14 (2H, q, J=7.3 Hz), 4.62 (2H, s), 7.18-7.23 (1H, dd, J=4.6 Hz, 7.9 Hz), 7.26-7.29 (6H, m), 7.49-7.64 (3H, m), 8.50-8.53 (1H, dd, J=2.0 Hz, 7.9 Hz), 8.55-8.57 (1H, dd, J=2.0 Hz, 4.9 Hz)

Synthetic Example 27

4-hydroxy-3-[1-oxo-2-(4-fluorophenyl)ethyl]-1-phenyl-1,8-naphthyridin-2 (1H)-one

The procedure of Synthetic Example 14 was repeated using 4-fluorophenylacetyl chloride in place of 3-methoxyphenylacetyl chloride to obtain 4-hydroxy-3-[1-oxo-2-(4-fluorophenyl)ethyl]-1-phenyl-1,8-naphthyridin-2 (1H)-one (43%), mp 185-187° C.

$^1$H NMR(CDCl$_3$) δ:4.61 (2H, s), 6.70-7.62 (2H, app-t, J=8.6 Hz), 7.19-7.28 (5H, m), 7.52-7.65 (3H, m), 8.51-8.57 (2H, m)

Synthetic Example 28

4-hydroxy-3-[1-oxo-2-(4-methylthiophenyl)ethyl]-1-phenyl-1,8-naphthyridin-2 (1H)-one

The procedure of Synthetic Example 14 was repeated using 4-methylthiophenylacetyl chloride in place of 3-methoxyphenylacetyl chloride to obtain 4-hydroxy-3-[1-oxo-2-(4-methylthiophenyl)ethyl]-1-phenyl-1,8-naphthyridin-2 (1H)-one (49%), mp 177-182° C.

$^1$H NMR(CDCl$_3$) δ:2.47 (3H, s), 4.60 (2H, s), 7.19-7.29 (7H, m), 7.49-7.64 (3H, m), 8.50-8.53 (1H, dd, J=2.0 Hz, 7.9 Hz), 8.55-8.58 (1H, dd, J=2.0 Hz, 4.6 Hz)

Synthetic Example 29

1-(3-cyanophenyl)-4-hydroxy-3-(1-oxo-2-phenylethyl)-1,8-naphthyridin-2 (1H)-one

(1) To methyl 2-(3-cyanophenylamino)nicotinate (507 mg, 2.0 mmol; synthesized according to WO, A, 01/42244) was added DMF (2 ml) and butyl acetate (2 ml) to form a solution at 80° C. To the solution was added potassium t-butoxide (449 mg, 4.0 mmol), and the mixture was stirred at about 130° C. overnight, evaporated while heating, and allowed to stand until it was cooled. The resulting residue was dissolved in water, partitioned with xylene, and washed. The resultant aqueous layer was acidified with hydrochloric acid, and filtered off to give precipitates which were washed with water and dried to afford a mixture containing 1-(3-cyanophenyl)-4-hydroxy-1,8-naphthyridin-2 (1H)-one (321 mg, 61%).

mp 287-288(dec.)° C. $^1$H NMR(DMSO-d$_6$) δ:5.94 (1H, s), 7.30 (1H, dd, J=4.8 Hz, 7.9 Hz), 7.64 (1H, dt, J=8.1 Hz, 1.5 Hz), 7.71 (1H, t, J=8.1 Hz), 7.84-7.86 (1H, m), 7.91 (1H, dt, J=7.4 Hz, 1.5 Hz), 8.29 (1H, dd, J=1.8 Hz, 7.7 Hz), 8.42 (1H, dd, J=1.8 Hz, 4.8 Hz)

(2) To a suspension of a mixture containing 1-(3-cyanophenyl)-4-hydroxy-1,8-naphthyridin-2 (1H)-one (958 mg, 3.64 mmol) in DMF (16 ml) was added sodium hydride (about 60%, 350 mg, 8.74 mmol, 2.4 eq.), and the mixture was stirred until the production of hydrogen was completed. Next, after phenylacetyl chloride (563 mg, 3.64 mmol, 1.0 eq.) was added, the mixture was stirred at room temperature, admixed with water, acidified with hydrochloric acid, filtered off to give precipitates which were washed with water. The resultant residue was purified by flash column chromatography to afford 1-(3-cyanophenyl)-4-hydroxy-3-(1-oxo-2-phenylethyl)-1,8-naphthyridin-2 (1H)-one (341 mg, 25%).

mp 216-218° C. $^1$H NMR(CDCl$_3$) δ:4.60 (2H, s), 7.23-7.35 (6H, m), 7.52-7.60 (2H, m), 7.70 (1H, t, J=7.9 Hz), 7.80 (1H, dt, J=7.9 Hz, 1.3 Hz), 8.50-8.52 (1H, m), 8.54 (1H, dd, J=2.0 Hz, 5.6 Hz)

Synthetic Example 30

4-hydroxy-3-(1-oxo-4-phenylbutyl)-1-phenyl-1,8-naphthyridin-2 (1H)-one

The procedure of Synthetic Example 5 was repeated using phenylbutylyl chloride in place of phenylacetyl chloride to afford 4-hydroxy-3-(1-oxo-4-phenylbutyl)-1-phenyl-1,8-naphthyridin-2 (1H)-one (yield for 2 steps: 49%).

mp 200.5-201.5° C. $^1$H NMR(CDCl$_3$) δ:1.99-2.10 (2H, m), 2.66-2.72 (2H, m), 3.34 (2H, t, J=7.6 Hz), 7.12-7.29 (8H, m), 7.47-7.62 (3H, m), 8.52 (1H, dd, J=2.0 Hz, 7.9 Hz), 8.55 (1H, dd, J=2.0 Hz, 4.9 Hz)

Synthetic Example 31

1-(3-fluorophenyl)-4-hydroxy-1,8-naphthyridin-2 (1H)-one (1) To a solution of methyl 2-(3-fluorophenylamino)-nicotinate (4.90 g, 16.2 mmol; synthesized according to WO, A, 01/42244) in 1,2-dichloroethane (80 ml) was added at 80° C. trichloromethyl chloroformate (also called: diphosgene, 5.9 ml, 48.3 mmol) gradually dropwise over about 30 minutes. Three hours later, activated carbon (130 mg) was added, and the mixture was heated under reflux for 30 minutes, filtered off, and then evaporated. The resultant residue was washed with isopropyl ether, and dried to give 1-(3-fluorophenyl)-2H-pyrido[2,3-d][1,3]oxazin-2,4(1H)-dione(3.42g, 82%) as crystals.

mp 164-166° C. $^1$H NMR(CDCl$_3$) δ:7.07-7.12 (1H, app-td, J=8.4 Hz, 2.0 Hz), 7.14-7.17 (1H, m), 7.22-7.28 (1H, m), 7.29-7.33 (1H, app-dd, J=4.8 Hz, 7.7 Hz), 7.51-7.59 (1H, app-dt, J=6.1 Hz, 8.4 Hz), 8.47-8.51 (1H, app-dd, J=2.0 Hz, 7.7 Hz), 8.58-8.60 (1H, app-dd, J=2.0 Hz, 4.9 Hz)

(2) To a solution of diethyl malonate (1.50 g, 9.3 mmol) in dimethylacetamide (14 ml) was added sodium hydride (about 60%, 467 mg, 11.65 mmol), and the mixture was stirred to form a solution until the production of hydrogen was completed. To the resulting solution was added 1-(3-fluorophenyl)-2H-pyrido[2,3-d][1,3]oxazin-2,4(1H)-dione (2.36 g, 9.15 mmol) while ice-cooling, and the mixture was stirred at 150° C. for 1 hour, cooled to room temperature, treated with ethyl acetate, allowed to stand. The resultant precipitate was collected by filtration, and washed with ethyl acetate, filtered off to give a residue which was dissolved in water, acidified to pH1 with hydrochloric acid to form precipitates. The resultant precipitate was collected by filtration, washed with water, and dried to afford 3-ethoxycarbonyl-1-(3-fluorophenyl)-4-hydroxy-1,8-naphthyridin-2(1H)(2.66 g, 88%) as crystals.

mp 187-189° C. $^1$H NMR(CDCl$_3$) δ: 1.44 (3H, t, J=7.1 Hz), 4.48 (2H, q, J=7.1 Hz), 6.97-7.02 (1H, m), 7.03-7.07 (1H, app-dq, J=7.7 Hz, 1.0 Hz), 7.14-7.24 (2H, m), 7.46-7.55 (1H, m), 8.47-8.50 (1H, app-dd, J=2.0 Hz, 7.9 Hz), 8.54-8.56 (1H, app-dd, J=2.0 Hz, 4.6 Hz), 14.47 (1H, s)

(3) To 3-ethoxycarbonyl-1-(3-fluorophenyl)-4-hydroxy-1,8-naphthyridin-2 (1H)-one (328 mg, 11.0 mmol) was added an aqueous solution (7 ml) of potassium hydroxide (560 mg, 10.0 mmol), and the mixture was heated under reflux overnight, acidified to pH1 with conc. hydrochloric acid, refluxed for 1 hour, filtered off to give precipitates which were washed with water and dried to afford 1-(3-fluorophenyl)-4-hydroxy-1,8-naphthyridin-2 (1H)-one (194.5 mg, 76%) as crystals.

mp 272° C.(dec.) $^1$H NMR(DMSO-d$_6$) δ: 5.94 (1H, s), 7.06-7.10 (1H, m), 7.16-7.21 (1H, app-dt, J=9.9 Hz, 1.8 Hz), 7.24-7.31 (2H, m), 7.48-7.57 (1H, m), 8.25-8.29 (1H, app-dd, J=1.8 Hz, 7.9 Hz), 8.41-8.43 (1H, app-dd, J=1.8 Hz, 7.9 Hz), 11.91 (1H, s)

Examples

Disclosed herein below are examples which are merely illustrative of the present invention and should not be construed as limiting the scope of the invention. It should be noted that the present invention encompasses various embodiments.

Example 1

5-phenyl-3-[2-(pyridin-4-yl)ethyl]-1H-pyrazolo[4,3-c][1,8]-naphthyridin-4 (5H)-one To a suspension of 4-hydroxy-3-[1-oxo-3-(pyridin-4-yl) propyl]-1-phenyl-1,8-naphthyridin-2 (1H)-one (50 mg, 0.13 mmol, prepared in Synthetic Example 1) in ethanol (1 ml) was added hydrazine monohydrate (80%, 20 μl, 0.50 mmol, 3.7 eq.) and the resultant mixture was heated under reflux overnight. The liquid reaction mixture was cooled to room temperature, and then filtered to give precipitates which were dried to obtain 5-phenyl-3-[2-(pyridin-4-yl)ethyl]-1H-pyrazolo[4,3-c][1,8]-naphthyridin-4 (5H)-one (40 mg, 81%).

mp 267-269° C. $^1$H NMR(DMSO-d$_6$) δ:3.06-3.12 (2H, m), 3.26-3.33 (2H, m), 7.23-7.29 (4H, m), 7.31-7.36 (1H, app-dd, J=4.6 Hz, 7.6 Hz), 7.41-7.56 (3H, m), 8.35-8.38 (1H, app-dd, J=1.3 Hz, 4.3 Hz), 8.43-8.45 (2H, app-d, J=5.9 Hz), 8.47-8.51 (1H, app-dd, J=1.7 Hz, 7.6 Hz), approximately 14 (1H, brs)

Example 2

1-methyl-5-phenyl-3-[2-(pyridin-4-yl) ethyl]-1H-pyrazolo-[4,3-c][1,8]-naphthyridin-4 (5H)-one To a suspension of 4-hydroxy-3-[1-oxo-3-(pyridin-4-yl) propyl]-1-phenyl-1,8-naphthyridin-2 (1H)-one (100 mg, 0.27 mmol, prepared in Synthetic Example 1) in ethanol (2 ml) was added methylhydrazine (40 μl, 0.75 mmol, 2.8 eq.) and the mixture was stirred at room temperature to form a solution which was then stirred for 30 minutes. After it was perceived that precipitation started, the mixture was heated under reflux for 3 hours and cooled to room temperature. Next, to the liquid mixture was added additional methylhydrazine (40 μl, 0.75 mmol, 2.8 eq.) and the resultant mixture was heated overnight with stirring at 70° C. The liquid reaction mixture was cooled to room temperature, and then filtered to give precipitates which were dried to obtain 1-methyl-5-phenyl-3-[2-(pyridin-4-yl)ethyl]-1H-pyrazolo[4,3-c][1,8]naphthyridin-4 (5H)-one (94 mg, 92%).

mp 285-286° C. ¹H NMR(CDCl₃) δ:3.11-3.17 (2H, m), 3.35-3.41 (2H, m), 4.36 (3H, s), 7.21-7.31 (5H, m), 7.48-7.65 (3H, m), 8.36-8.40 (1H, app-dd, J=1.7 Hz, 7.9 Hz), 8.44-8.48 (3H, m)

Example 3

5-phenyl-3-[2-(pyridin-3-yl)ethyl]-1H-pyrazolo[4,3-c][1,8]-naphthyridin-4 (5H)-one The procedure of Example 1 was repeated using a suspension of 4-hydroxy-3-[1-oxo-3-(pyridin-3-yl)propyl]-1-phenyl-1,8-naphthyridin-2 (1H)-one (50 mg, 0.14 mmol, prepared in Synthetic Example 2) in ethanol (10 ml), and hydrazine monohydrate (80%, 20 μl, 0.50 mmol, 3.7 eq.), to obtain 5-phenyl-3-[2-(pyridin-3-yl)ethyl]-1H-pyrazolo[4,3-c][1,8]-naphthyridin-4 (5H)-one (yield: 78%).

mp 322° C.(dec.) ¹H NMR(DMSO-d₆) δ:3.08 (2H, t, J=8.3 Hz), 7.27-7.36 (4H, m), 7.44-7.55 (3H, m), 7.61-7.64 (1H, app-d, J=7.6 Hz), 8.36-8.41 (3H, m), 8.47-8.51 (1H, app-dd, J=1.7 Hz, 7.6 Hz)

Example 4

5-phenyl-3-(pyridin-3-yl)methyl-1H-pyrazolo[4,3-c][1,8]-naphthyridin-4 (5H)-one

The procedure of Example 1 was repeated using a suspension of 4-hydroxy-3-[1-oxo-2-(pyridin-3-yl)ethyl]-1-phenyl-1,8-naphthyridin-2 (1H)-one (16 mg, 0.045 mmol, prepared in Synthetic Example 3) in ethanol (5 ml), and hydrazine monohydrate (80%, 10 μl, 0.25 mmol, 5.5 eq.) to obtain 5-phenyl-3-(pyridin-3-yl)methyl-1H-pyrazolo[4,3-c][1,8]-naphthyridin-4 (5H)-one (yield: 76%).

mp 306° C.(dec.) ¹H NMR(DMSO-d₆) δ:4.38 (2H, s), 7.24-7.54 (7H, m), 7.70-7.73 (1H, m), 8.36-8.38 (1H, app-dd, J=1.7 Hz, 5.0 Hz), 8.40-8.42 (1H, app-m), 8.49-8.52 (1H, app-dd, J=1.7 Hz, 7.6H), 8.56-8.57 (1H, app-d, J=2.3 Hz)

Example 5

5-phenyl-3-[2-(1-oxypyridin-4-yl)ethyl]-1H-pyrazolo[4,3-c][1,8]-naphthyridin-4 (5H)-one To a solution of 5-phenyl-3-[2-(pyridin-4-yl)ethyl]-1H-pyrazolo[4,3-c][1,8]-naphthyridin-4 (5H)-one (100 mg, 0.27 mmol, prepared in Example 1) in chloroform (80 ml) was added a solution of m-chloroperbenzoic acid (mCPBA, 70%, 67 mg, 0.27 mmol, 1.0 eq.) in chloroform (1 ml) at room temperature, and the mixture was stirred. One hour later, an additional solution of mCPBA (70%, 31 mg, 0.13 mmol, 0.5 eq.) in chloroform (1 ml) was added, and the mixture was stirred for additional 2 hours. To the resultant liquid reaction mixture was added saturated aqueous sodium hydrogen carbonate and the mixture was stirred, then filtered to give precipitates which were subjected to recrystallization with DMF, and dried to give 5-phenyl-3-[2-(1-oxypyridin-4-yl)ethyl]-1H-pyrazolo[4,3-c][1,8]-naphthyridin-4 (5H)-one (58 mg, 55%).

mp 285° C.(dec.)/DMF ¹H NMR(DMSO-d₆) δ:3.02-3.07 (2H, m), 3.20-3.26 (2H, m), 7.22-7.27 (5H, m), 7.38-7.54 (3H, m), 8.06-8.08 (2H, app-d, J=6.9 Hz), 8.25-8.27 (1H, app-dd, J=1.7 Hz, 4.6 Hz), 8.46-8.50 (1H, app-dd, J=2.0 Hz, 7.6 Hz)

Example 6

5-(3-nitrophenyl)-3-[2-(pyridin-4-yl)ethyl]-1H-pyrazolo[4,3-c][1,8]naphthyridin-4 (5H)-one To a suspension of 4-hydroxy-1-(3-nitrophenyl)-3-[1-oxo-3-(pyridin-4-yl)propyl]-1,8-naphthyridin-2 (1H)-one (416 mg, 1.0 mmol, prepared in Synthetic Example 4) in ethanol (15 ml) was added hydrazine monohydrate (80%, 180 μl, 4.5 mmol, 4.5 eq.), and the resultant mixture was treated in the same manner as in Example 1 to give 5-(3-nitrophenyl)-3-[2-(pyridin-4-yl)ethyl]-1H-pyrazolo[4,3-c][1,8]naphthyridin-4 (5H)-one (394 mg, 96%).

mp 161-165° C. ¹H NMR(DMSO-d₆) δ:3.06-3.12 (2H, m), 3.27-3.30 (2H, m), 7.24-7.26 (2H, app-dd, J=1.7 Hz, 4.6 Hz), 7.35-7.39 (1H, app-dd, J=4.9 Hz, 7.9 Hz), 7.83-7.85 (2H, m), 8.28-8.38 (3H, m), 8.43-8.45 (2H, app-dd, J=1.7 Hz, 4.3 Hz), 8.50-8.53 (1H, app-dd, J=2.0 Hz, 7.9 Hz)

Example 7

5-(3-nitrophenyl)-3-[2-(1-oxypyridin-4-yl)ethyl]-1H-pyrazolo[4,3-c][1,8]naphthyridin-4 (5H)-one To 5-(3-nitrophenyl)-3-[2-(pyridin-4-yl)ethyl]-1H-pyrazolo[4,3-c][1,8]naphthyridin-4 (5H)-one (300 mg, 0.73 mmol, prepared in Example 6) was added chloroform (250 ml), and mixture was heated to form a solution. After it was perceived that the mixture was a solution when cooled to room temperature, a solution of mCPBA (about 70%, 269 mg, 1.09 mmol, 1.5 eq.) in chloroform (3 ml) was added dropwise. One hour later, an additional solution of mCPBA (about 70%, 90 mg, 0.37 mmol, 0.5 eq.) in chloroform (1 ml) was added and the mixture was stirred for 1.5 hours. To the resulting reaction suspension was added saturated aqueous sodium hydrogen carbonate and it was stirred, and filtered off to remove insolubles. The precipitates were washed with DMF under heating, filtered off, and dried to give 5-(3-nitrophenyl)-3-[2-(1-oxypyridin-4-yl)ethyl]-1H-pyrazolo[4,3-c][1,8]naphthyridin-4 (5H)-one (283 mg, 91%).

mp 328° C.(dec.) ¹H NMR(DMSO-d₆) δ:3.06 (2H, t, J=7.6 Hz), 3.27 (2H, t, J=7.6 Hz), 7.22-7.24 (2H, app-d, J=6.9 Hz), 7.35-7.40 (1H, app-dd, J=5.3 Hz, 7.6 Hz), 7.80-7.87 (2H, m), 8.07-8.10 (2H, app-d, J=6.9 Hz), 8.28-8.38 (3H, m), 8.50-8.53 (2H, app-dd, J=2.0 Hz, 7.9 Hz), 14.04 (1H, br)

Example 8

5-(3-aminophenyl)-3-[2-(pyridin-4-yl)ethyl]-1H-pyrazolo[4,3-c][1,8]naphthyridin-4 (5H)-one To a solution of 5-(3-nitrophenyl)-3-[2-(pyridin-4-yl)ethyl]-1H-pyrazolo[4,3-c][1,8]naphthyridin-4 (5H)-one (150 mg, 0.36 mmol, prepared in Example 6) in conc. hydrochloric acid (3 ml) was added tin chloride.2H₂O (450 mg, 3-fold weights) and the mixture was stirred overnight, then treated with saturated aqueous sodium hydrogen carbonate to make it to pH8-9, and extracted with chloroform 4 times. The resulting organic layer was washed with saturated aqueous sodium chloride, dried over anhydrous magnesium sulfate, and evaporated to give a residue (about 110 mg). The residue was recrystallized from DMF to afford 5-(3-aminophenyl)-

3-[2-(pyridin-4-yl)ethyl]-1H-pyrazolo[4,3-c][1,8]naphthyridin-4 (5H)-one (16.3 mg, 12%).

mp 261-263° C./DMF $^1$H NMR(DMSO-d$_6$) δ:3.06-3.12 (2H, m), 3.26-3.29 (2H, m), 5.18 (2H, brs), 6.34-6.38 (1H, m), 6.39-6.41 (1H, app-t, J=2.0 Hz), 6.61-6.65 (1H, m), 7.10-7.16 (1H, app-t, J=7.9 Hz), 7.24-7.26 (2H, app-d, J=5.9 Hz), 7.30-7.34 (1H, app-dd, J=4.6 Hz, 7.6 Hz), 8.39-8.48 (4H, m), 13.97 (1H, br)

Example 9

3-benzyl-5-phenyl-1H-pyrazolo[4,3-c][1,8]naphthyridin-4 (5H)-one

To a suspension of 4-hydroxy-3-(1-oxo-2-phenylethyl)-1-phenyl-1,8-naphthyridin-2 (1H)-one (2.33 g, 6.54 mmol, prepared in Synthetic Example 5) in DMF (50 ml) was added hydrazine monohydrate (80%, 970 μl, 24.21 mmol, 3.7 eq.) and the mixture was then stirred at 100 to 110° C. for 4 hours, admixed with water to precipitate crystals, and allowed to stand until it was cooled. Next, the cooled mixture was filtered, washed with water, and dried to give 3-benzyl-5-phenyl-1H-pyrazolo[4,3-c][1,8]naphthyridin-4 (5H)-one (1.90 g, 82%).

mp 305-308° C./DMF-H$_2$O $^1$H NMR(DMSO-d$_6$) δ:4.36 (2H, s), 7.15-7.36 (8H, m), 7.40-7.55 (3H, m), 8.35 (1H, dd, J=1.7 Hz, 4.6 Hz), 8.50 (1H, dd, J=1.6 Hz, 7.6 Hz)

Example 10

5-phenyl-3-(2-phenylethyl)-1H-pyrazolo[4,3-c][1,8]-naphthyridin-4 (5H)-one

To a suspension of 4-hydroxy-3-(1-oxo-3-phenylpropyl)-1-phenyl-1,8-naphthyridin-2 (1H)-one (110 mg, 0.30 mmol, prepared in Synthetic Example 6) in ethanol (6 ml) was added hydrazine monohydrate (80%, 44 μl, 1.1 mmol, 3.7 eq.), and the mixture was treated in the same manner as in Example 1 to give 5-phenyl-3-(2-phenylethyl)-1H-pyrazolo[4,3-c][1,8]naphthyridin-4 (5H)-one (80 mg, 73%).

mp 248-250° C. $^1$H NMR(DMSO-d$_6$) δ:3.02-3.08 (2H, m), 3.23-3.29 (2H, m), 7.14-7.35 (8H, m), 7.41-7.56 (3H, m), 8.36 (1H, dd, J=2.0 Hz, 4.6 Hz), 8.49 (1H, dd, J=1.6 Hz, 7.6 Hz), 14 (1H, br)

Example 11

3-[2-(4-nitrophenyl)ethyl]-5-phenyl-1H-pyrazolo[4,3-c][1,8]naphthyridin-4 (5H)-one To a suspension of 4-hydroxy-3-[1-oxo-3-(4-nitrophenyl)propyl]-1-phenyl-1,8-naphthyridin-2 (1H)-one (104 mg, 0.25 mmol, prepared in Synthetic Example 7) in DMF (2 ml) was added hydrazine monohydrate (80%, 40 μl, 11.0 mmol, 4.0 eq.), and the mixture was treated in the same manner as in Example 9 to give 3-[2-(4-nitrophenyl)ethyl]-5-phenyl-1H-pyrazolo[4,3-c][1,8]naphthyridin-4 (5H)-one (100 mg, 97%).

mp 260-262° C./DMF-H$_2$O $^1$H NMR(DMSO-d$_6$) δ:3.17-3.03 (4H, m), 7.25-7.29 (2H, m), 7.34 (1H, dd, J=4.6 Hz, 7.6 Hz), 7.41-7.56 (3H, m), 7.49-7.52 (2H, app-d, J=8.9 Hz), 8.12-8.16 (2H, app-d, J=8.6 Hz), 8.37 (1H, dd, J=1.7 Hz, 4.6 Hz), 8.49 (1H, dd, J=1.7 Hz, 7.6 Hz), 14 (1H, br)

Example 12

3-[2-(4-cyanophenyl)ethyl]-5-phenyl-1H-pyrazolo[4,3-c][1,8]-naphthyridin-4 (5H)-one To a suspension of 4-hydroxy-3-[1-oxo-3-(4-cyanophenyl)propyl]-1-phenyl-1,8-naphthyridin-2 (1H)-one (270 mg, 0.69 mmol, prepared in Synthetic Example 8) in DMF (5 ml) was added hydrazine monohydrate (80%, 102 μl, 2.55 mmol, 3.7 eq.), and the mixture was treated in the same manner as in Example 9 to give 3-[2-(4-cyanophenyl)ethyl]-5-phenyl-1H-pyrazolo[4,3-c][1,8]naphthyridin-4 (5H)-one (243 mg, 90%).

mp 267-269° C./DMF-H$_2$O $^1$H NMR(DMSO-d$_6$) δ:3.12-3.18 (2H, m), 3.25-3.32 (2H, m), 7.25-7.29 (2H, m), 7.33 (1H, dd, J=4.6 Hz, 7.6 Hz), 7.41-7.44 (2H, app-d, J=8.3 Hz), 7.41-7.56 (3H, m), 7.72-7.75 (2H, app-d, J=8.3 Hz), 8.37 (1H, dd, J=1.3 Hz, 4.6 Hz), 8.50 (1H, dd, J=1.6 Hz, 7.6 Hz), 14 (1H, br)

Example 13

3-[2-(4-aminophenyl)ethyl]-5-phenyl-1H-pyrazolo[4,3-c][1,8]naphthyridin-4 (5H)-one To a solution of 3-[2-(4-nitrophenyl)ethyl]-5-phenyl-1H-pyrazolo[4,3-c][1,8]naphthyridin-4 (5H)-one (131 mg, 0.32 mmol, prepared in Example 11) in DMF (4 ml) and methanol (4 ml) was added activated carbon-palladium (13 mg), and the mixture was stirred under hydrogen atmosphere for 3.5 hours, and filtered. After methanol was distilled off, the resultant solution was admixed with water, and filtered to give precipitates which were dried to afford 3-[2-(4-aminophenyl)ethyl]-5-phenyl-1H-pyrazolo[4,3-c][1,8]naphthyridin-4 (5H)-one (113 mg, 93%).

mp >310° C./DMF-H$_2$O $^1$H NMR(DMSO-d$_6$) δ:2.82-2.89 (2H, m), 3.17 (2H, br), 4.84 (2H, brs), 6.45-6.48 (2H, app-d, J=8.2 Hz), 6.86-6.89 (2H, app-d, J=7.9 Hz), 7.25-7.29 (3H, m), 7.41-7.56 (3H, m), 8.35 (1H, br), 8.48 (1H, dd, J=1.3 Hz, 7.6 Hz), 14 (1H, br)

Example 14

3-[2-(4-carboxyphenyl)ethyl]-5-phenyl-1H-pyrazolo[4,3-c][1,8]naphthyridin-4 (5H)-one To a solution of 3-[2-(4-cyanophenyl)ethyl]-5-phenyl-1H-pyrazolo[4,3-c][1,8]naphthyridin-4 (5H)-one (100 mg, 0.26 mmol, prepared in Example 12) in DMSO (2 ml) was added 50% sulfuric acid (2 ml) and the mixture was heated under reflux for 2 hours. To the resultant reaction mixture was added water, and precipitates were filtered off, and dried to give 3-[2-(4-carboxyphenyl)ethyl]-5-phenyl-1H-pyrazolo[4,3-c][1,8]naphthyridin-4 (5H)-one (107 mg, quantitative yield).

mp 318-320° C./DMF-H$_2$O $^1$H NMR(DMSO-d$_6$) δ:3.10-3.31 (4H, m), 7.26-7.55 (8H, m), 7.83-7.86 (2H, app-d, J=8.2 Hz), 8.36 (1H, br), 8.49 (1H, d, J=6.9 Hz), 12.82 (1H, br), 14 (1H, br)

Example 15

3-[2-(3-nitrophenyl)ethyl]-5-phenyl-1H-pyrazolo[4,3-c][1,8]naphthyridin-4 (5H)-one To a suspension of 4-hydroxy-3-[1-oxo-3-(3-nitrophenyl)propyl]-1-phenyl-1,8-naphthyridin-2 (1H)-one (415 mg, 11.0 mmol, prepared in Synthetic Example 9) in DMF (10 ml)

was added hydrazine monohydrate (80%, 160 μl, 3.99 mmol, 4.0 eq.), and the mixture was then stirred at 100 to 110° C. for 7 hours. The reaction mixture was admixed with water to precipitate crystals, allowed to stand until it was cooled, filtered off, washed with water, and dried to give 3-[2-(3-nitrophenyl)ethyl]-5-phenyl-1H-pyrazolo[4,3-c][1,8]naphthyridin-4 (5H)-one (389 mg, 94%).

mp 245-247° C./DMF-H$_2$O $^1$H NMR(DMSO-d$_6$) δ:3.22-3.33 (4H, m), 7.26-7.28 (2H, m), 7.31-7.36 (1H, app-dd, J=4.6, 7.6 Hz), 7.44-7.59 (4H, m), 7.67-7.70 (1H, app-d, J=7.6 Hz), 8.05-8.10 (2H, m), 8.35-8.38 (1H, m), 8.47-8.50 (1H, app-dd, J=2.0 Hz, 7.6 Hz), 14.01 (1H, s)

Example 16

3-[2-(2-nitrophenyl)ethyl]-5-phenyl-1H-pyrazolo[4,3-c][1,8]naphthyridin-4 (5H)-one To a suspension of 4-hydroxy-3-[1-oxo-3-(2-nitrophenyl)propyl]-1-phenyl-1,8-naphthyridin-2 (1H)-one (837 mg, 2.0 mmol, prepared in Synthetic Example 10) in DMF (20 ml) was added hydrazine monohydrate (80%, 350 μl, 8.74 mmol, 4.4 eq.), and the mixture was then stirred at 100 to 110° C. overnight. The reaction mixture was admixed with water to precipitate crystals, allowed to stand until it was cooled, filtered off, washed with water, and dried to give 3-[2-(2-nitrophenyl)ethyl]-5-phenyl-1H-pyrazolo[4,3-c][1,8]naphthyridin-4 (5H)-one (790 mg, 95%).

mp 333-335° C./DMF-H$_2$O $^1$H NMR(DMSO-d$_6$) δ:3.32 (4H, m), 7.25-7.28 (2H, m), 7.31-7.36 (1H, app-dd, J=4.6, 7.6 Hz), 7.44-7.62 (6H, m), 7.90-7.93 (1H, m), 8.36-8.37 (1H, m), 8.47-8.51 (1H, app-dd, J=2.0 Hz, 7.6 Hz), 14.01 (1H, s)

Example 17

3-[2-(2-cyanophenyl)ethyl]-5-phenyl-1H-pyrazolo[4,3-c][1,8]naphthyridin-4 (5H)-one To a suspension of 4-hydroxy-3-[1-oxo-3-(2-cyanophenyl)propyl]-1-phenyl-1,8-naphthyridin-2 (1H)-one (991 mg, 2.51 mmol, prepared in Synthetic Example 11) in DMF (25 ml) was added hydrazine monohydrate (80%, 371 μl, 9.26 mmol, 3.7 eq.), and the mixture was treated in the same manner as in Example 16 to give 3-[2-(2-cyanophenyl)ethyl]-5-phenyl-1H-pyrazolo[4,3-c][1,8]naphthyridin-4 (5H)-one (953 mg, 97%).

mp 315.5-316.5° C./DMF-H$_2$O $^1$H NMR(DMSO-d$_6$) δ:3.2-3.5 (4H, m), 7.24-7.27 (2H, app-d, J=7.9 Hz), 7.31-7.63 (7H, m), 7.73-7.75 (1H, d, J=7.6 Hz), 8.36-8.38 (1H, m), 8.46-8.50 (1H, m)

Example 18

3-[2-(3-cyanophenyl)ethyl]-5-phenyl-1H-pyrazolo[4,3-c][1,8]naphthyridin-4 (5H)-one To a suspension of 4-hydroxy-3-[1-oxo-3-(3-cyanophenyl)propyl]-1-phenyl-1,8-naphthyridin-2 (1H)-one (495 mg, 1.25 mmol, prepared in Synthetic Example 12) in DMF (12 ml) was added hydrazine monohydrate (80%, 148 μl, 3.69 mmol, 3.0 eq.), and the mixture was treated in the same manner as in Example 16 to give 3-[2-(3-cyanophenyl)ethyl]-5-phenyl-1H-pyrazolo[4,3-c][1,8]naphthyridin-4 (5H)-one (456 mg, 93%).

mp 219.5-224.5° C./DMF-H$_2$O $^1$H NMR(DMSO-d$_6$) δ:3.10-3.15 (2H, m), 3.26-3.29 (2H, m), 7.26-7.29 (2H, m), 7.31-7.36 (1H, dd, J=4.9 Hz, 7.6 Hz), 7.41-7.58 (5H, m), 7.64-7.70 (2H, m), 8.35-8.38 (1H, dd, J=1.7 Hz, 4.9 Hz), 8.47-8.51 (1H, dd, J=1.7 Hz, 7.9 Hz), approximately 14 (1H, br)

Example 19

3-(2-(4-methylphenyl)ethyl)-5-phenyl-1H-pyrazolo[4,3-c][1,8]naphthyridin-4 (5H)-one To a suspension of 4-hydroxy-3-[1-oxo-3-(4-methylphenyl)propyl]-1-phenyl-1,8-naphthyridin-2 (1H)-one (362 mg, 0.94 mmol, prepared in Synthetic Example 13) in DMF (10 ml) was added hydrazine monohydrate (80%, 150 μl, 3.74 mmol, 4.0 eq.), and the mixture was then stirred at 100 to 130° C. for 2 hours. The reaction mixture was admixed with water to precipitate crystals, allowed to stand until it was cooled, filtered off, washed with water, and dried to give 3-[(2-(4-methylphenyl)ethyl]-5-phenyl-1H-pyrazolo[4,3-c][1,8]naphthyridin-4 (5H)-one (335 mg, 94%).

mp 264-265° C./DMF-H$_2$O $^1$H NMR(DMSO-d$_6$) δ:2.25 (3H, s), 2.99 (2H, t, J=8.6 Hz), 3.23 (1H, t, J=8.6 Hz), 7.06-7.13 (4H, m), 7.26-7.35 (3H, m), 7.42-7.55 (3H, m), 8.35-8.37 (1H, m), 8.47-8.51 (1H, app-dd, J=1.7 Hz, 7.6 Hz), 13.98 (1H, s)

Example 20

3-(3-methoxybenzyl)-5-phenyl-1H-pyrazolo[4,3-c][1,8]naphthyridin-4 (5H)-one

To a suspension of 4-hydroxy-3-[1-oxo-2-(3-methoxyphenyl)ethyl]-1-phenyl-1,8-naphthyridin-2 (1H)-one (50 mg, 0.13 mmol, prepared in Synthetic Example 14) in DMF (1 ml) was added hydrazine monohydrate (80%, 20 μl, 0.50 mmol, 3.8 eq.), and the mixture was treated in the same manner as in Example 16 to give 3-(3-methoxybenzyl)-5-phenyl-1H-pyrazolo[4,3-c][1,8]naphthyridin-4 (5H)-one (41 mg, 83%).

mp 234-236° C./DMF-H$_2$O $^1$H NMR(DMSO-d$_6$) δ:3.69 (3H, s), 4.32 (2H, s), 6.75-6.78 (1H, app-d, J=7.8 Hz), 6.88-6.93 (2H, m), 7.16-7.21 (1H, app-t, J=7.9 Hz), 7.25-7.27 (2H, m), 7.30-7.35 (1H, app-dd, J=5.0 Hz, 7.9 Hz), 7.44-7.54 (3H, m), 8.35-8.36 (1H, m), 8.48-8.51 (1H, app-dd, J=2.0 Hz, 7.9 Hz)

Example 21

3-(4-methoxybenzyl)-5-phenyl-1H-pyrazolo[4,3-c][1,8]naphthyridin-4 (5H)-one

To a suspension of 4-hydroxy-3-[1-oxo-2-(4-methoxyphenyl)ethyl]-1-phenyl-1,8-naphthyridin-2 (1H)-one (50 mg, 0.13 mmol, prepared in Synthetic Example 15) in DMF (1 ml) was added hydrazine monohydrate (80%, 1 ml, 24.96 mmol, 192 eq.), and the mixture was treated in the same manner as in Example 16 to give 3-(4-methoxybenzyl)-5-phenyl-1H-pyrazolo[4,3-c][1,8]naphthyridin-4 (5H)-one (44 mg, 89%).

mp 300-302° C./DMF-H$_2$O $^1$H NMR(DMSO-d$_6$) δ:3.69 (3H, s), 4.28 (2H, s), 6.81-6.85 (2H, app-d, J=8.6 Hz), 7.24-7.27 (4H, app-d, J=8.6 Hz), 7.29-7.34 (1H, app-dd, J=5.0 Hz, 7.9 Hz), 7.41-7.54 (3H, m), 8.33-8.36 (1H, app-dd, J=1.7 Hz, 5.0 Hz), 8.47-8.51 (1H, app-dd, J=1.7 Hz, 7.9 Hz)

Example 22

3-(2-methoxybenzyl)-5-phenyl-1H-pyrazolo[4,3-c][1,8]naphthyridin-4 (5H)-one

To a suspension of 4-hydroxy-3-[1-oxo-2-(2-methoxyphenyl)ethyl]-1-phenyl-1,8-naphthyridin-2 (1H)-one (121 mg, 0.31 mmol, prepared in Synthetic Example 16) in DMF (3 ml) was added hydrazine monohydrate (80%, 50 μl, 1.25 mmol, 4.0 eq.), and the mixture was treated in the same manner as in Example 16 to give 3-(2-methoxybenzyl)-5-phenyl-1H-pyrazolo[4,3-c][1,8]naphthyridin-4 (5H)-one (111 mg, 93%).

mp 276-277° C./DMF-$H_2O$ $^1H$ NMR(DMSO-$d_6$) δ:3.80 (3H, s), 4.31 (2H, s), 6.78-6.85 (1H, m), 6.96-7.03 (2H, m), 7.14-7.34 (4H, m), 7.42-7.53 (3H, m), 8.33-8.35 (1H, app-dd, J=1.4 Hz, 4.6 Hz), 8.49-8.52 (1H, app-dd, J=1.4 Hz, 7.6 Hz)

Example 23

3-(2-thienylmethyl)-5-phenyl-1H-pyrazolo[4,3-c][1,8]naphthyridin-4 (5H)-one

To a suspension of 4-hydroxy-3-[1-oxo-2-(2-thienyl)ethyl]-1-phenyl-1,8-naphthyridin-2 (1H)-one (30 mg, 0.08 mmol, prepared in Synthetic Example 17) in DMF (1.5 ml) was added hydrazine monohydrate (80%, 30 μl, 0.75 mmol, 9.4 eq.), and the mixture was treated in the same manner as in Example 16 to give 3-(2-thienylmethyl)-5-phenyl-1H-pyrazolo[4,3-c][1,8]naphthyridin-4 (5H)-one (22 mg, 72%).

mp 282-284° C./DMF-$H_2O$ $^1H$ NMR(DMSO-$d_6$) δ:4.53 (3H, s), 6.90-6.99 (2H, m), 7.25-7.55 (7H, m), 8.39-8.52 (2H, m), 14.18 (1H, s)

Example 24

3-(4-nitrobenzyl)-5-phenyl-1H-pyrazolo[4,3-c][1,8]naphthyridin-4 (5H)-one

To a suspension of 4-hydroxy-3-[1-oxo-2-(4-nitrophenyl)ethyl]-1-phenyl-1,8-naphthyridin-2 (1H)-one (304 mg, 0.76 mmol, prepared in Synthetic Example 18) in DMF (7.5 ml) was added hydrazine monohydrate (80%, 108 μl, 2.70 mmol, 3.6 eq.), and the mixture was then stirred at 100 to 110° C. for 5 hours. The reaction mixture was admixed with water to precipitate crystals, allowed to stand until it was cooled, filtered off, washed with water, and dried to give 3-(4-nitrobenzyl)-5-phenyl-1H-pyrazolo[4,3-c][1,8]-naphthyridin-4 (5H)-one (260 mg, 86%).

mp 254-255° C./DMF-$H_2O$ $^1H$ NMR(DMSO-$d_6$) δ:4.49 (2H, s), 7.24-7.27 (2H, app-d, J=8.2 Hz), 7.33-7.37 (1H, dd, J=4.6 Hz, 7.9 Hz), 7.40-7.54 (5H, m), 7.57-7.60 (2H, app-d, J=8.2 Hz), 8.14-8.17 (2H, app-d, J=7.9 Hz), 8.37-8.38 (1H, d, J=4.9 Hz), 8.50-8.52 (1H, dd, J=7.6 Hz)

Example 25

3-(3-nitrobenzyl)-5-phenyl-1H-pyrazolo[4,3-c][1,8]naphthyridin-4 (5H)-one

To a suspension of 4-hydroxy-3-[1-oxo-2-(3-nitrophenyl)ethyl]-1-phenyl-1,8-naphthyridin-2 (1H)-one (568 mg, 1.42 mmol, prepared in Synthetic Example 19) in DMF (14 ml) was added hydrazine monohydrate (80%, 203 μl, 5.07 mmol, 3.6 eq.), and the mixture was treated in the same manner as in Example 24 to give 3-(3-nitrobenzyl)-5-phenyl-1H-pyrazolo[4,3-c][1,8]naphthyridin-4 (5H)-one (397 mg, 71%).

mp >320° C./DMF-$H_2O$ $^1H$ NMR(DMSO-$d_6$) δ:4.51 (2H, s), 7.25-7.28 (2H, m), 7.33-7.37 (1H, dd, J=4.6 Hz, 7.6 Hz), 7.41-7.63 (4H, m), 7.79-7.81 (1H, d, J=7.9 Hz), 8.06-8.10 (1H, m), 8.20 (1H, s), 8.37-8.39 (1H, dd, J=2.0 Hz, 4.9 Hz), 8.49-8.53 (1H, dd, J=2.0 Hz, 7.9 Hz), approximately 14.2 (1H, br)

Example 26

3-(2-nitrobenzyl)-5-phenyl-1H-pyrazolo[4,3-c][1,8]naphthyridin-4 (5H)-one

To a suspension of 4-hydroxy-3-[1-oxo-2-(2-nitrophenyl)ethyl]-1-phenyl-1,8-naphthyridin-2 (1H)-one (643 mg, 1.60 mmol, prepared in Synthetic Example 20) in DMF (16 ml) was added hydrazine monohydrate (80%, 230 μl, 5.74 mmol, 3.6 eq.), and the mixture was treated in the same manner as in Example 24 to give 3-(2-nitrobenzyl)-5-phenyl-1H-pyrazolo[4,3-c][1,8]naphthyridin-4 (5H)-one (541 mg, 85%).

mp 318-320° C. (dec.)/DMF-$H_2O$ $^1H$ NMR(DMSO-$d_6$) δ:4.69 (2H, s), 7.25-7.28 (2H, m), 7.34-7.38 (1H, dd, J=4.6 Hz, 7.6 Hz), 7.43-7.55 (5H, m), 7.63-7.68 (1H, td, J=7.6 Hz, 1.3 Hz), 7.99-8.02 (1H, dd, J=1.3 Hz, 8.2 Hz), 8.38-8.40 (1H, dd, J=1.7 Hz, 4.6 Hz), 8.47-8.51 (1H, dd, J=1.7 Hz, 7.6 Hz), approximately 14 (1H, br)

Example 27

3-(2,5-dimethoxybenzyl)-5-phenyl-1H-pyrazolo[4,3-c][1,8]naphthyridin-4 (5H)-one

To a suspension of 4-hydroxy-3-[1-oxo-2-(2,5-dimethoxyphenyl)ethyl]-1-phenyl-1,8-naphthyridin-2 (1H)-one (200 mg, 0.48 mmol, prepared in Synthetic Example 21) in DMF (5 ml) was added hydrazine monohydrate (80%, 100 μl, 2.50 mmol, 5.2 eq.), and the mixture was treated in the same manner as in Example 16 to give 3-(2,5-dimethoxybenzyl)-5-phenyl-1H-pyrazolo[4,3-c][1,8]naphthyridin-4 (5H)-one (162 mg, 82%).

mp 248-250° C./DMF-$H_2O$ $^1H$ NMR(DMSO-$d_6$) δ:3.61 (3H, s), 3.75 (3H, s), 4.29 (2H, s), 6.64-6.66 (1H, app-d, J=3.0 Hz), 6.73-6.78 (1H, app-dd, J=3.0 Hz, 8.9 Hz), 6.88-6.91 (1H, app-d, J=8.9 Hz), 7.24-7.54 (6H, m), 8.35-8.37 (1H, m), 8.49-8.52 (1H, app-dd, J=1.6 Hz, 7.6 Hz), 13.98 (1H, s)

Example 28

3-(3,4-dimethoxybenzyl)-5-phenyl-1H-pyrazolo[4,3-c][1,8]naphthyridin-4 (5H)-one

To a suspension of 4-hydroxy-3-[1-oxo-2-(3,4-dimethoxyphenyl)ethyl]-1-phenyl-1,8-naphthyridin-2 (1H)-one (200 mg, 0.48 mmol, prepared in Synthetic Example 22) in DMF (5 ml) was added hydrazine monohydrate (80%, 100 μl, 2.50 mmol, 5.2 eq.), and the mixture was treated in the same manner as in Example 16 to give 3-(3,4-dimethoxybenzyl)-5-phenyl-1H-pyrazolo[4,3-c][1,8]naphthyridin-4 (5H)-one (159 mg, 80%).

mp 230-232° C./DMF-$H_2O$ $^1H$ NMR(DMSO-$d_6$) δ:3.68 (6H, s), 4.28 (2H, s), 6.83 (2H, app-s), 7.03 (1H, app-s), 7.25-7.55 (6H, m), 8.34-8.35 (1H, m), 8.48-8.50 (1H, m), 14.08 (1H, s)

Example 29

3-(3,5-dimethoxybenzyl)-5-phenyl-1H-pyrazolo[4,3-c][1,8]naphthyridin-4 (5H)-one

To a suspension of 4-hydroxy-3-[1-oxo-2-(3,5-dimethoxyphenyl)ethyl]-1-phenyl-1,8-naphthyridin-2 (1H)-one (200 mg, 0.48 mmol, prepared in Synthetic Example 23) in DMF (5 ml) was added hydrazine monohydrate (80%, 100 μl, 2.50 mmol, 5.2 eq.), and the mixture was treated in the same manner as in Example 16 to give 3-(3,5-dimethoxybenzyl)-5-phenyl-1H-pyrazolo[4,3-c][1,8]naphthyridin-4 (5H)-one (179 mg, 90%).

mp 258-259° C./DMF-$H_2O$ $^1H$ NMR(DMSO-$d_6$) δ:3.68 (6H, s), 4.27 (2H, s), 6.31-6.35 (2H, m), 6.51-6.52 (2H, app-d, J=2.0 Hz), 7.25-7.53 (6H, m), 8.34-8.36 (1H, m), 8.48-8.51 (1H, m)

Example 30

3-(2,4-dimethoxybenzyl)-5-phenyl-1H-pyrazolo[4,3-c][1,8]naphthyridin-4 (5H)-one

To a suspension of 4-hydroxy-3-[1-oxo-2-(2,4-dimethoxyphenyl)ethyl]-1-phenyl-1,8-naphthyridin-2 (1H)-one (100 mg, 0.24 mmol, prepared in Synthetic Example 24) in DMF (2 ml) was added hydrazine monohydrate (80%, 50 μl, 1.25 mmol, 5.2 eq.), and the mixture was treated in the same manner as in Example 24 to give 3-(2,4-dimethoxybenzyl)-5-phenyl-1H-pyrazolo[4,3-c][1,8]naphthyridin-4 (5H)-one (87 mg, 87%).

mp 266-267° C./DMF-$H_2O$ $^1H$ NMR(DMSO-$d_6$) δ:3.72 (3H, s), 3.78 (3H, s), 4.23 (2H, s), 6.39-6.43 (1H, app-dd, J=2.3 Hz, 8.3 Hz), 6.53-6.54 (1H, app-d, J=2.3 Hz), 6.95-6.98 (1H, app-d, J=8.3 Hz), 7.24-7.27 (2H, m), 7.29-7.34 (1H, app-dd, J=4.6 Hz, 7.6 Hz), 7.40-7.54 (3H, m), 8.34-8.35 (1H, m), 8.48-8.51 (1H, app-dd, J=1.7 Hz, 7.6 Hz)

Example 31

3-(4-cyanobenzyl)-5-phenyl-1H-pyrazolo[4,3-c][1,8]naphthyridin-4 (5H)-one

To a suspension of 4-hydroxy-3-[1-oxo-2-(4-cyanophenyl)ethyl]-1-phenyl-1,8-naphthyridin-2 (1H)-one (265 mg, 0.69 mmol, prepared in Synthetic Example 25) in DMF (7 ml) was added hydrazine monohydrate (80%, 82 μl, 2.05 mmol, 3.0 eq.), and the mixture was treated in the same manner as in Example 16 to give 3-(4-cyanobenzyl)-5-phenyl-1H-pyrazolo[4,3-c][1,8]naphthyridin-4 (5H)-one (190 mg, 73%).

mp 316-318° C. (dec.)/DMF-$H_2O$ $^1H$ NMR(DMSO-$d_6$) δ:4.36-4.54 (2H, m), 7.85-7.20 (10H, m), 8.30-8.55 (2H, m), approximately 14.2 (1H, br)

Example 32

3-(4-ethoxycarbonylmethylbenzyl)-5-phenyl-1H-pyrazolo[4,3-c][1,8]naphthyridin-4 (5H)-one To a suspension of 4-hydroxy-3-[1-oxo-2-(4-ethoxycarbonylmethylphenyl)ethyl]-1-phenyl-1,8-naphthyridin-2 (1H)-one (128 mg, 0.29 mmol, prepared in Synthetic Example 26) in DMF (3 ml) was added hydrazine monohydrate (80%, 34 μl, 0.87 mmol, 3.0 eq.), and the mixture was treated in the same manner as in Example 16 to give 3-(4-ethoxycarbonylmethylbenzyl)-5-phenyl-1H-pyrazolo[4,3-c][1,8]naphthyridin-4 (5H)-one (115 mg, 91%).

mp 263-264° C./DMF-$H_2O$ $^1H$ NMR(DMSO-$d_6$, measuring temperature: 80° C.) δ:1.16 (3H, t, J=7.3 Hz), 3.56 (2H, s), 4.05 (2H, q, J=7.3 Hz), 4.35 (2H, brs), 7.13-7.53 (10H, m), 8.31-8.33 (1H, dd, J=1.3 Hz, 4.6 Hz), 8.46-8.50 (1H, dd, J=1.7 Hz, 7.6 Hz), 13.89 (1H, br)

Example 33

3-(4-fluorobenzyl)-5-phenyl-1H-pyrazolo[4,3-c][1,8]naphthyridin-4 (5H)-one

To a suspension of 4-hydroxy-3-[1-oxo-2-(4-fluorophenyl)ethyl]-1-phenyl-1,8-naphthyridin-2 (1H)-one (3.2 g, 8.5 mmol, prepared in Synthetic Example 27) in DMF (50 ml) was added hydrazine monohydrate (80%, 1.2 ml, 30 mmol, 3.5 eq.), and the mixture was then stirred at 130° C. for 2 hours. The reaction mixture was admixed with water to precipitate crystals, allowed to stand until it was cooled, filtered off, washed with water, and dried to give 3-(4-fluorobenzyl)-5-phenyl-1H-pyrazolo[4,3-c][1,8]naphthyridin-4 (5H)-one (3.1 g, 98%).

mp 271-274° C./DMF-$H_2O$ $^1H$ NMR(DMSO-$d_6$) δ:4.34 (2H, s), 7.07-7.13 (2H, m), 7.25-7.55 (8H, m), 8.35-8.37 (1H, app-dd, J=2.0 Hz, 5.0 Hz), 8.48-8.51 (1H, app-dd, J=2.0 Hz, 7.9 Hz), 14.10 (1H, s)

Example 34

3-(4-methylsulfonylbenzyl)-5-phenyl-1H-pyrazolo[4,3-c][1,8]naphthyridin-4 (5H)-one (1) To a solution of 4-hydroxy-3-[1-oxo-2-(4-methylthiophenyl)ethyl]-1-phenyl-1,8-naphthyridin-2 (1H)-one (201 mg, 0.5 mmol, prepared in Synthetic Example 28) in chloroform (10 ml) was added mCPBA (123 mg, 1.0 eq.) while ice-cooling, and the mixture was stirred for 1 hour. Thereafter, mCPBA (additional total: 285 mg, 1.5 eq.) was added, and the mixture was stirred for 1.5 hours, admixed with saturated aqueous sodium hydrogen carbonate and extracted with chloroform. The organic layer was dried over anhydrous magnesium sulfate, evaporated, and purified by flash column chromatography to afford 4-hydroxy-3-[1-oxo-2-(4-methylsulfonylphenyl)ethyl]-1-phenyl-1,8-naphthyridin-2 (1H)-one (112 mg, 52%).

mp 260-262° C. $^1H$ NMR(CDCl$_3$) δ:3.05 (3H, s), 4.73 (2H, s), 7.20-7.25 (1H, dd, J=4.6 Hz, 7.6 Hz), 7.25-7.29 (2H, m), 7.48-7.64 (5H, m), 7.88-7.93 (2H, app-d, J=8.6 Hz), 8.51-8.55 (1H, dd, J=2.0 Hz, 7.9 Hz), 8.57-8.59 (1H, dd, J=2.0 Hz, 4.6 Hz)

(2) To a suspension of 4-hydroxy-3-[1-oxo-2-(4-methylsulfonylphenyl)ethyl]-1-phenyl-1,8-naphthyridin-2 (1H)-one (101 mg, 0.23 mmol) in DMF (2.5 ml) was added hydrazine monohydrate (80%, 28 μl, 0.87 mmol, 3.8 eq.), and the mixture was treated in the same manner as in Example 16 to give 3-(4-methylsulfonylbenzyl)-5-phenyl-1H-pyrazolo[4,3-c][1,8]naphthyridin-4 (5H)-one (72 mg, 72%).

mp 311.5-312.5° C./DMF-$H_2O$ $^1H$ NMR(DMSO-$d_6$) δ:3.16 (3H, s), 4.47 (2H, s), 7.24-7.28 (2H, m), 7.32-7.37 (1H, dd, J=4.6 Hz, 7.6 Hz), 7.40-7.55 (3H, m), 7.57-7.60 (2H, app-d, J=8.2 Hz), 7.82-7.85 (2H, app-d, J=8.6 Hz), 8.36-8.38 (1H, dd, J=1.6 Hz, 4.6 Hz), 8.49-8.53 (1H, dd, J=1.7 Hz, 7.6 Hz), approximately 14.2 (1H, br)

Example 35

3-[2-(3-aminophenyl)ethyl]-5-phenyl-1H-pyrazolo[4,3-c][1,8]naphthyridin-4 (5H)-one To a solution of 3-[2-(3-nitrophenyl)ethyl]-5-phenyl-1H-pyrazolo[4,3-c][1,8]naphthyridin-4 (5H)-one (216 mg, 0.52 mmol, prepared in Example 15) in DMF (5 ml) and methanol (5 ml) was added activated carbon-palladium (22 mg), and the mixture was stirred overnight under hydrogen atmosphere, and filtered. After methanol was distilled off, the resultant solution was admixed with water, and filtered to give precipitates which were dried to afford 3-[2-(3-aminophenyl)ethyl]-5-phenyl-1H-pyrazolo[4,3-c][1,8]-naphthyridin-4 (5H)-one (189 mg, 94%).

mp 229-231° C./DMF-$H_2O$ $^1H$ NMR(DMSO-$d_6$) δ:2.86-2.89 (2H, m), 3.18-3.20 (2H, m), 4.96 (2H, s), 6.35-6.38 (2H, m), 6.46 (1H, app-s), 6.87-6.93 (1H, app-t, J=7.8 Hz), 7.27-7.55 (6H, m), 8.34-8.38 (1H, m), 8.48-8.50 (1H, m), 14.00 (1H, s)

Example 36

3-[2-(2-aminophenyl)ethyl]-5-phenyl-1H-pyrazolo[4,3-c][1,8]naphthyridin-4 (5H)-one To a solution of 3-[2-(2-nitrophenyl)ethyl]-5-phenyl-1H-pyrazolo[4,3-c][1,8]naphthyridin-4 (5H)-one (420 mg, 11.0 mmol, prepared in Example 16) in DMF (45 ml) and methanol (20 ml) was added activated carbon-palladium (45 mg), and the mixture was stirred overnight under hydrogen atmosphere, and filtered. After methanol was distilled off, the resultant solution was admixed with water, and filtered to give precipitates which were dried to afford 3-[2-(2-aminophenyl)ethyl]-5-phenyl-1H-pyrazolo[4,3-c][1,8]-naphthyridin-4 (5H)-one (364 mg, 94%).

mp 289-291° C./DMF-$H_2O$ $^1H$ NMR(DMSO-$d_6$) δ:2.80-2.89 (2H, m), 3.09-3.15 (2H, m), 5.17 (2H, s), 6.44-6.49 (1H, m), 6.56-6.59 (1H, m), 6.88-6.96 (2H, m), 7.29-7.37 (3H, m), 7.42-7.56 (3H, m), 8.37-8.39 (1H, m), 8.50-8.54 (1H, app-dd, J=1.7 Hz, 7.6 Hz), 14.02 (1H, s)

Example 37

3-[2-(2-carboxyphenyl)ethyl]-5-phenyl-1H-pyrazolo[4,3-c][1,8]naphthyridin-4 (5H)-one To a solution of 3-[2-(2-cyanophenyl)ethyl]-5-phenyl-1H-pyrazolo[4,3-c][1,8]naphthyridin-4 (5H)-one (202 mg, 0.52 mmol, prepared in Example 17) in DMSO (20 ml) was added 50% sulfuric acid (10 ml), and the mixture was heated under reflux overnight. The resultant reaction mixture was admixed with water, and filtered to give precipitates which were dried to afford 3-[2-(2-carboxyphenyl)ethyl]-5-phenyl-1H-pyrazolo[4,3-c][1,8]naphthyridin-4 (5H)-one (94 mg, 44%).

mp 302-308° C./DMF-$H_2O$ $^1H$ NMR(DMSO-$d_6$) δ:3.28-3.43 (4H, m), 7.26-7.55 (9H, m), 7.79-7.81 (1H, d, J=7.6 Hz), 8.35 (1H, br), 8.48-8.50 (1H, d, J=7.3 Hz), approximately 12.9 (1H, br), approximately 13.9 (1H, br)

Example 38

3-[2-(3-carboxyphenyl)ethyl]-5-phenyl-1H-pyrazolo[4,3-c][1,8]naphthyridin-4 (5H)-one To a solution of 3-[2-(3-cyanophenyl)ethyl]-5-phenyl-1H-pyrazolo[4,3-c][1,8]naphthyridin-4 (5H)-one (300 mg, 0.77 mmol, prepared in Example 18) in DMSO (30 ml) was added 50% sulfuric acid (15 ml), and the mixture was heated under reflux overnight. The reaction mixture was admixed with water, and filtered to give precipitates which were dried to afford 3-[2-(3-carboxyphenyl)ethyl]-5-phenyl-1H-pyrazolo[4,3-c][1,8]naphthyridin-4 (5H)-one (87 mg, 28%).

mp 159-161° C./DMF $^1H$ NMR(DMSO-$d_6$) δ:3.09-3.15 (2H, m), 3.26-3.29 (2H, m), 7.26-7.56 (8H, m), 7.75-7.78 (1H, d, J=7.3 Hz), 7.82 (1H, s), 8.35-8.37 (1H, d, J=3.6 Hz), 8.47-8.51 (1H, dd, J=1.3 Hz, 7.6 Hz), approximately 14 (1H, br)

Example 39

3-(4-carboxybenzyl)-5-phenyl-1H-pyrazolo[4,3-c][1,8]-naphthyridin-4 (5H)-one

To a solution of 3-(4-cyanobenzyl)-5-phenyl-1H-pyrazolo[4,3-c][1,8]naphthyridin-4 (5H)-one (180 mg, 0.48 mmol, prepared in Example 31) in DMSO (18 ml) was added 50% sulfuric acid (10 ml), and the mixture was stirred at 140° C. After water (5 ml) was added, the mixture was heated under reflux, admixed with additional water (5 ml), and heated under reflux for totally 3 hours. The reaction mixture was admixed with water, and filtered to give precipitates which were dried to afford 3-(4-carboxybenzyl)-5-phenyl-1H-pyrazolo[4,3-c][1,8]naphthyridin-4 (5H)-one (106 mg, 56%).

mp >320° C./DMF-$H_2O$ $^1H$ NMR(DMSO-$d_6$) δ:4.42 (2H, s), 7.25-7.54 (8H, m), 7.83-7.86 (2H, app-d, J=7.9 Hz), 8.35-8.37 (1H, m), 8.49-8.52 (1H, dd, J=1.3 Hz, 7.3 Hz), approximately 12.8 (1H, br), approximately 14.2 (1H, br)

Example 40

3-(3-hydroxybenzyl)-5-phenyl-1H-pyrazolo[4,3-c][1,8]-naphthyridin-4 (5H)-one

To a solution of 3-(3-methoxybenzyl)-5-phenyl-1H-pyrazolo[4,3-c][1,8]naphthyridin-4 (5H)-one (53 mg, 0.14 mmol, prepared in Example 20) in acetic acid (2 ml) was added 47% hydrogen bromide (1.5 ml), and the mixture was heated under reflux overnight. The reaction mixture was admixed with water, and filtered to give precipitates which were dried to afford 3-(3-hydroxybenzyl)-5-phenyl-1H-pyrazolo[4,3-c][1,8]naphthyridin-4 (5H)-one (39 mg, 76%).

mp 276-278° C. $^1H$ NMR(DMSO-$d_6$) δ:4.26 (2H, s), 6.54-6.58 (1H, m), 6.72-6.77 (2H, m), 7.02-7.08 (1H, app-t, J=7.9 Hz), 7.25-7.28 (2H, m), 7.30-7.35 (1H, app-dd, J=4.6 Hz, 7.9 Hz), 7.41-7.55 (3H, m), 8.34-8.37 (1H, app-dd, J=1.7 Hz, 4.6 Hz), 8.48-8.52 (1H, app-dd, 1.6 Hz, 7.9 Hz), 9.29 (1H, s)

Example 41

3-(4-hydroxybenzyl)-5-phenyl-1H-pyrazolo[4,3-c][1,8]-naphthyridin-4 (5H)-one

To a solution of 3-(4-methoxybenzyl)-5-phenyl-1H-pyrazolo[4,3-c][1,8]naphthyridin-4 (5H)-one (100 mg, 0.26 mmol, prepared in Example 21) in acetic acid (1 ml) was added 47% hydrogen bromide (44 μl), and the mixture was heated under reflux. After additional 47% hydrogen bromide (144 μl) was added, the mixture was heated under reflux overnight. The reaction mixture was admixed with water, and filtered to give precipitates which were dried to afford 3-(4-hydroxybenzyl)-5-phenyl-1H-pyrazolo[4,3-c][1,8]-naphthyridin-4 (5H)-one (92.1 mg, 96%).

mp 316-317° C. $^1$H NMR(DMSO-d$_6$) δ:4.23 (2H, s), 6.63-6.67 (2H, app-d, J=8.6 Hz), 7.11-7.14 (2H, app-d, J=8.6 Hz), 7.25-7.34 (3H, m), 7.44-7.55 (3H, m), 8.34-8.36 (1H, m), 8.47-8.51 (1H, app-dd, J=2.0 Hz, 7.6 Hz), 9.22 (1H, s), 14.2 (1H, s)

Example 42

3-(2-hydroxybenzyl)-5-phenyl-1H-pyrazolo[4,3-c][1,8]-naphthyridin-4 (5H)-one

To a solution of 3-(2-methoxybenzyl)-5-phenyl-1H-pyrazolo[4,3-c][1,8]naphthyridin-4 (5H)-one (50 mg, 0.13 mmol, prepared in Example 22) in acetic acid (1 ml) was added 47% hydrogen bromide (0.5 ml), and the mixture was heated under reflux. After additional 47% hydrogen bromide (1 ml) and acetic acid (1 ml) was added, the mixture was heated under reflux for 2 days, then admixed with water, filtered to give precipitates which were dried to afford 3-(2-hydroxybenzyl)-5-phenyl-1H-pyrazolo[4,3-c][1,8]-naphthyridin-4 (5H)-one (31 mg, 64%).

mp 278-280° C. $^1$H NMR(DMSO-d$_6$) δ:4.30 (2H, s), 6.65-6.70 (1H, app-t, J=7.9 Hz), 6.79-6.82 (1H, app-d, J=8.3 Hz), 6.94-7.05 (2H, m), 7.24-7.27 (2H, app-d, J=8.1 Hz), 7.30-7.35 (1H, m), 7.40-7.54 (3H, m), 8.34-8.36 (1H, m), 8.50-8.52 (1H, m)

Example 43

3-(4-aminobenzyl)-5-phenyl-1H-pyrazolo[4,3-c][1,8]-naphthyridin-4 (5H)-one

To a solution of 3-(4-nitrobenzyl)-5-phenyl-1H-pyrazolo[4,3-c][1,8]naphthyridin-4 (5H)-one (200 mg, 0.50 mmol, prepared in Example 24) in DMF (10 ml) and methanol (10 ml) was added activated carbon-palladium (20 mg), the mixture was stirred under hydrogen atmosphere for 3 days, and filtered. After methanol was distilled off, the resultant solution was admixed with water, and filtered to give precipitates which were dried to afford 3-(4-aminobenzyl)-5-phenyl-1H-pyrazolo[4,3-c][1,8]naphthyridin-4 (5H)-one (120 mg, 65%).

mp 210-212° C. (dec.)/DMF-H$_2$O $^1$H NMR(DMSO-d$_6$) δ:4.16 (2H, s), 4.89 (2H, brs), 6.44-6.47 (2H, app-d, J=8.2 Hz), 6.97-7.00 (2H, app-d, J=8.6 Hz), 7.23-7.33 (3H, m), 7.40-7.55 (3H, m), 8.32-8.35 (1H, dd, J=1.7 Hz, 4.6 Hz), 8.46-8.50 (1H, dd, J=1.6 Hz, 7.6 Hz), approximately 14 (1H, br)

Example 44

3-(3-aminobenzyl)-5-phenyl-1H-pyrazolo[4,3-c][1,8]-naphthyridin-4 (5H)-one

To a solution of 3-(3-nitrobenzyl)-5-phenyl-1H-pyrazolo[4,3-c][1,8]naphthyridin-4 (5H)-one (273 mg, 0.69 mmol, prepared in Example 25) in DMF (14 ml) and methanol (14 ml) was added activated carbon-palladium (27 mg), the mixture was stirred under hydrogen atmosphere overnight, and filtered. After methanol was distilled off, the resultant solution was admixed with water, and filtered to give precipitates which were dried to afford 3-(3-aminobenzyl)-5-phenyl-1H-pyrazolo[4,3-c][1,8]naphthyridin-4 (5H)-one (220 mg, 87%).

mp 286.5-288.5° C.(dec.)/DMF-H$_2$O $^1$H NMR(DMSO-d$_6$) δ:4.20 (2H, s), 4.98 (2H, s), 6.35-6.38 (1H, d, J=8.6 Hz), 6.46-6.49 (2H, m), 6.86-6.92 (1H, t, J=7.9 Hz), 7.25-7.28 (2H, d, J=7.6 Hz), 7.29-7.34 (1H, dd, J=4.9 Hz, 7.6 Hz), 7.41-7.54 (3H, m), 8.34-8.35 (1H, d, J=3.3 Hz), 8.48-8.51 (1H, dd, J=1.3 Hz, 7.6 Hz), approximately 14 (1H, brs)

Example 45

3-(2-aminobenzyl)-5-phenyl-1H-pyrazolo[4,3-c][1,8]-naphthyridin-4 (5H)-one

To a solution of 3-(2-nitrobenzyl)-5-phenyl-1H-pyrazolo[4,3-c][1,8]naphthyridin-4 (5H)-one (376 mg, 0.95 mmol, prepared in Example 26) in DMF (20 ml) and methanol (20 ml) was added activated carbon-palladium (38 mg), the mixture was stirred under hydrogen atmosphere overnight, and filtered. After methanol was distilled off, the resultant solution was admixed with water, and filtered to give precipitates which were dried to afford 3-(2-aminobenzyl)-5-phenyl-1H-pyrazolo[4,3-c][1,8]naphthyridin-4 (5H)-one (349 mg, 100%).

mp >320° C.(dec.)/DMF-H$_2$O $^1$H NMR(DMSO-d$_6$) δ:4.17 (2H, s), 5.19 (2H, brs), 6.45-6.51 (1H, td, J=7.6 Hz, 1.3 Hz), 6.57-6.61 (1H, dd, J=1.0 Hz, 7.9 Hz), 6.87-6.93 (1H, td, J=7.6 Hz, 1.3 Hz), 7.04-7.08 (1H, dd, J=1.3 Hz, 7.6 Hz), 7.24-7.28 (2H, m), 7.31-7.36 (1H, dd, J=4.6 Hz, 7.6 Hz), 7.41-7.56 (3H, m), 8.35-8.38 (1H, dd, J=1.7 Hz, 4.6 Hz), 8.49-8.53 (1H, dd, J=1.7 Hz, 7.6 Hz), approximately 14 (1H, brs)

Example 46

3-(4-carboxymethylbenzyl)-5-phenyl-1H-pyrazolo[4,3-c][1,8]naphthyridin-4 (5H)-one 3-(4-Ethoxycarbonylmethylbenzyl)-5-phenyl-1H-pyrazolo[4,3-c][1,8]naphthyridin-4 (5H)-one (110 mg, 0.25 mmol, prepared in Example 32) was dissolved in DMSO (3 ml) at 50° C., admixed with 50% sulfuric acid (2 ml) at 100° C., and then heated under reflux for 1 hour. The reaction mixture was admixed with water, and filtered to give precipitates which were dried to afford 3-(4-carboxymethylbenzyl)-5-phenyl-1H-pyrazolo[4,3-c][1,8]naphthyridin-4 (5H)-one (96 mg, 93%).

mp 297-300° C. $^1$H NMR(DMSO-d$_6$) δ:3.49 (2H, s), 4.33 (2H, brs), 7.14-7.34 (7H, m), 7.40-7.55 (3H, m), 8.36 (1H, br), 8.47-8.51 (1H, dd, J=1.7 Hz, 7.6 Hz), approximately 12.3 (1H, br), 14.11 (1H, br)

Example 47

3-(4-acetoxybenzyl)-5-phenyl-1H-pyrazolo[4,3-c][1,8]-naphthyridin-4 (5H)-one

To a solution of 3-(4-hydroxybenzyl)-5-phenyl-1H-pyrazolo [4,3-c][1,8]naphthyridin-4 (5H)-one (192 mg, 0.52 mmol, prepared in Example 41) in DMF (2 ml) was added a solution of 1-acetylimidazole (114 mg, 1.04 mmol, 2 eq.) in DMF (2 ml) while ice-cooling, and the mixture was stirred overnight at room temperature, and then diluted with aqueous sodium hydrogen carbonate. Precipitates were filtered off, and the mixture was dried and purified by flash column chromatography to afford 3-(4-acetoxybenzyl)-5-phenyl-1H-pyrazolo[4,3-c][1,8]naphthyridin-4 (5H)-one (128 mg, 60%).

mp 278-282° C. $^1$H NMR(DMSO-d$_6$) δ:2.23 (3H, s), 4.36 (2H, s), 7.01-7.04 (2H, app-d, J=8.3 Hz), 7.26-7.54 (8H, m), 8.36-8.52 (2H, m), 14.16 (1H, s)

Example 48

3-[2-(4-methanesulfonylaminophenyl)ethyl]-5-phenyl-1H-pyrazolo[4,3-c][1,8]naphthyridin-4 (5H)-one To a solution of 3-[2-(4-aminophenyl)ethyl]-5-phenyl-1H-pyrazolo[4,3-c][1,8]naphthyridin-4 (5H)-one (38 mg, 0.10 mmol, prepared in Example 13) in pyridine (2 ml) was added methanesulfonyl chloride (18.5 mg, 0.16 mmol, 1.6 eq.), and the mixture was stirred at room temperature for 1 hour. The reaction mixture was admixed with water, and filtered to give precipitates which were dried to afford 3-[2-(4-methanesulfonylaminophenyl)ethyl]-5-phenyl-1H-pyrazolo[4,3-c][1,8]naphthyridin-4 (5H)-one (43 mg, 86%).

mp 284-285° C. $^1$H NMR(DMSO-d$_6$) δ:2.96 (3H, s), 3.18-3.26 (4H, m), 7.15-7.53 (10H, m), 8.34-8.51 (2H, m), 8.82 (1H, s), 13.80 (1H, s)

Example 49

3-(4-methanesulfonylaminobenzyl)-5-phenyl-1H-pyrazolo[4,3-c][1,8]naphthyridin-4 (5H)-one To a solution of 3-(4-aminobenzyl)-5-phenyl-1H-pyrazolo[4,3-c][1,8]naphthyridin-4 (5H)-one (107 mg, 0.29 mmol, prepared in Example 43) in pyridine (2 ml) was added methanesulfonyl chloride (47 mg, 0.41 mmol, 1.4 eq.), and the mixture was stirred at room temperature for 1 hour. The reaction mixture was admixed with water, and filtered to give precipitates which were dried and purified by flash column chromatography to afford 3-(4-methanesulfonylaminobenzyl)-5-phenyl-1H-pyrazolo[4,3-c][1,8]naphthyridin-4 (5H)-one (84 mg, 65%).

mp 306-307° C. $^1$H NMR(DMSO-d$_6$):2.93 (3H, s), 4.31 (2H, s), 7.09-7.12 (2H, app-d, J=8.3 Hz), 7.26-2.31 (5H, m), 7.44-7.54 (3H, m), 8.35-8.36 (1H, m), 8.48-8.51 (1H, app-dd, 2.0 Hz, 7.9 Hz), 9.60 (1H, s), 14.20 (1H, s)

Example 50

5-phenyl-3-[2-(2-ureidophenyl)ethyl]-1H-pyrazolo[4,3-c][1,8]naphthyridin-4 (5H)-one To a suspension of 3-[2-(2-aminophenyl)ethyl]-5-phenyl-1H-pyrazolo[4,3-c][1,8]naphthyridin-4 (5H)-one (38 mg, 0.09 mmol, prepared in Example 36) in a mixture solvent of acetic acid (1 mL) and water (1 mL) was added potassium cyanate (12 mg, 0.15 mmol, 1.7 eq) at room temperature. The mixture was stirred overnight at 35° C., and filtered to give precipitates which were washed with water and then dried to afford 5-phenyl-3-[2-(2-ureidophenyl)ethyl]-1H-pyrazolo[4,3-c][1,8]naphthyridin-4 (5H)-one (40 mg, 94%).

mp 300-305° C. $^1$H NMR(DMSO-d$_6$) δ:2.91-2.98 (2H, m), 3.10-3.14 (2H, m), 5.80 (2H, s), 6.87-6.92 (1H, m), 7.09-7.14 (1H, m), 7.16-7.19 (1H, m), 7.32-7.35 (2H, m), 7.38-7.42 (1H, app-dd, J=4.6 Hz, 7.3 Hz), 7.46-7.57 (3H, m), 7.93-7.96 (1H, app-d, J=8.3 Hz), 8.23 (1H, s), 8.42-8.43 (1H, m), 8.54-8.57 (1H, app-dd, 1.7 Hz, 7.9 Hz)

Example 51

3-benzyl-5-(4-methoxyphenyl)-1H-pyrazolo[4,3-c][1,8]-naphthyridin-4 (5H)-one

A suspension of 4-hydroxy-1-(4-methoxyphenyl)-1,8-naphthyridin-2 (1H)-one (1.07 g, 4.0 mmol; prepared according to JP, A, 61-246183 (1986) and/or J. Med. Chem., 31, 2108 (1988)) in DMF (4 ml) was added sodium hydride (about 60%, 352 mg, 8.8 mmol, 2.2 eq.), and the mixture was stirred until the production of hydrogen was completed. Next, after phenylacetyl chloride (0.63 ml, 4.8 mmol, 1.2 eq.) was added, the mixture was stirred at room temperature, admixed with water, acidified with hydrochloric acid, and then filtered off to give precipitates which were washed with water. The resulting precipitate was suspended in DMF (8 mL) without purification, treated with hydrazine monohydrate (80%, 513 μl, 12.8 mmol, 3.2 eq.), and the mixture was stirred at 100 to 110° C. for 2 hours. The reaction mixture was admixed with water, and filtered off to give precipitates which were dried to afford 3-benzyl-5-(4-methoxyphenyl)-1H-pyrazolo[4,3-c][1,8]naphthyridin-4 (5H)-one (826 mg, 54%).

mp >320° C./DMF-H$_2$O $^1$H NMR(DMSO-d$_6$) δ:3.83 (3H, s), 4.35 (2H, s), 7.01-7.07 (2H, app-d, J=9.1 Hz), 7.13-7.18 (2H, app-d, J=8.9 Hz), 7.19-7.35 (6H, m), 8.35 (1H, dd, J=1.8 Hz, 4.8 Hz), 8.48 (1H, dd, J=1.8 Hz, 7.7 Hz), 14.07 (1H, br)

Example 52

3-benzyl-5-(4-hydroxyphenyl)-1H-pyrazolo[4,3-c][1,8]-naphthyridin-4 (5H)-one

To a solution of 3-benzyl-5-(4-methoxyphenyl)-1H-pyrazolo[4,3-c][1,8]naphthyridin-4 (5H)-one (200 mg, 0.52 mmol, prepared in Example 51) in acetic acid (2 ml) was added 47% hydrogen bromide (1 ml), and the mixture was heated under reflux overnight. The reaction mixture was admixed with water, and filtered to give precipitates which were dried to afford 3-benzyl-5-(4-hydroxyphenyl)-1H-pyrazolo[4,3-c][1,8]naphthyridin-4 (5H)-one (165 mg, 86%).

mp >320° C. $^1$H NMR(DMSO-d$_6$) δ:4.35 (2H, s), 6.84-6.87 (2H, app-d, J=8.6 Hz), 6.99-7.02 (2H, app-d, J=8.6 Hz), 7.15-7.35 (6H, m), 8.35-8.37 (1H, m), 8.47 (1H, dd, J=1.8 Hz, 7.7 Hz), 9.57 (1H, brs), 14.08 (1H, br)

Example 53

3-benzyl-5-(3-cyanophenyl)-1H-pyrazolo[4,3-c][1,8]-naphthyridin-4 (5H)-one

To a suspension of 1-(3-cyanophenyl)-4-hydroxy-3-(1-oxo-2-phenylethyl)-1,8-naphthyridin-2 (1H)-one (314 mg, 0.82 mmol, prepared in Synthetic Example 29) in DMF (4 ml) was added hydrazine monohydrate (80%, 132 μl, 4.12 mmol, 4.0 eq.), and the mixture was stirred at 100 to 110° C. for 2 hours. The reaction mixture was admixed with water, and filtered to give precipitates which were washed with water and dried to afford 3-benzyl-5-(3-cyanophenyl)-1H-pyrazolo[4,3-c][1,8]naphthyridin-4 (5H)-one (287 mg, 92%).

mp 285-287° C.(dec.)/DMF-H$_2$O $^1$H NMR(DMSO-d$_6$) δ:4.36 (2H, s), 7.15-7.38 (6H, m), 7.71 (1H, dt, J=8.2 Hz, 1.8

Hz), 7.34 (1H, t, J=8.1 Hz), 7.91-7.95 (2H, m), 8.36 (1H, dd, J=1.6 Hz, 4.8 Hz), 8.51 (1H, dd, J=1.6 Hz, 7.7 Hz)

Example 54

3-benzyl-5-(3-carboxyphenyl)-1H-pyrazolo[4,3-c][1, 8]-naphthyridin-4 (5H)-one

To a solution of 3-benzyl-5-(3-cyanophenyl)-1H-pyrazolo [4,3-c][1,8]naphthyridin-4 (5H)-one (120 mg, 0.32 mmol, prepared in Example 53) in DMSO (15 ml) was added 50% sulfuric acid (5 ml), and the mixture was heated under reflux for 2.5 hours. The reaction mixture was admixed with water, and filtered to give precipitates which were dried to afford 3-benzyl-5-(3-carboxyphenyl)-1H-pyrazolo[4,3-c][1,8] naphthyridin-4 (5H)-one (73 mg, 58%).

mp 300-305° C. $^1$H NMR(DMSO-$d_6$) δ:4.32-4.39 (2H, m), 7.20-7.35 (6H, m), 7.55 (1H, dt, J=8.4 Hz, 1.8 Hz), 7.65 (1H, t, J=7.7 Hz), 7.80 (1H, t, J=1.6 Hz), 8.02 (1H, dt, J=7.7 Hz, 1.5 Hz), 8.35 (1H, br), 8.51 (1H, d, J=6.3 Hz), 13.05 (1H, br), 14.15 (1H, br)

Example 55

5-phenyl-3-(3-phenylpropyl)-1H-pyrazolo[4,3-c][1, 8]-naphthyridin-4 (5H)-one

To a suspension of 4-hydroxy-3-(1-oxo-4-phenylbutyl)-1-phenyl-1,8-naphthyridin-2 (1H)-one (384 mg, 11.0 mmol, prepared in Synthetic Example 30) in DMF (4 ml) was added hydrazine monohydrate (80%, 160 μl, 4.0 mmol, 4.0 eq.), and the mixture was stirred at 100 to 110° C. for 2 hours. The reaction mixture was admixed with water, and filtered to give precipitates which were washed with water and dried to afford 5-phenyl-3-(3-phenylpropyl)-1H-pyrazolo[4,3-c][1, 8]naphthyridin-4 (5H)-one (354 mg, 93%).

mp 202-203.5° C./DMF-H$_2$O $^1$H NMR(DMSO-$d_6$) δ:2.04 (2H, app-quin., J=7.6 Hz), 2.65 (2H, t, J=7.6 Hz), 3.01 (2H, t, J=7.9 Hz), 7.12-7.30 (7H, m), 7.31 (1H, dd, J=4.6 Hz, 7.6 Hz), 7.40-7.54 (3H, m), 8.34 (1H, dd, J=2.0 Hz, 4.9 Hz), 8.48 (1H, dd, J=2.0 Hz, 7.6 Hz), approximately 14 (1H, br)

Example 56

3-benzyl-5-(3-nitrophenyl)-1H-pyrazolo[4,3-c][1,8]-naphthyridin-4 (5H)-one

To a suspension of 4-hydroxy-1-(3-nitrophenyl)-1,8-naphthyridin-2 (1H)-one (1.13 g, 4 mmol, obtained in Synthetic Example 4 (3)) in DMF (16 ml) was added sodium hydride (about 60%, 384 mg, 9.6 mmol, 2.4 eq.), and the mixture was stirred until the production of hydrogen was completed. Next, after phenylacetyl chloride (742 mg, 4.8 mmol, 1.2 eq.) was added, the mixture was stirred at room temperature, followed by addition of water. After acidified with hydrochloric acid, it was filtered to give precipitates which were washed with water and suspended in DMF (16 mL) without further purification. To the suspension was added hydrazine monohydrate (80%, 448 μl, 11.2 mmol, 2.8 eq.), and the resultant mixture was stirred at 100 to 110° C. overnight. The reaction mixture was admixed with water, and filtered to give precipitates which were dried to afford 3-benzyl-5-(3-nitrophenyl)-1H-pyrazolo[4,3-c][1,8]naphthyridin-4 (5H)-one (714 mg, 45%).

mp 276-279° C./DMF-H$_2$O $^1$H NMR(DMSO-$d_6$, measuring temperature: 80° C.) δ:4.37 (2H, s), 7.16-7.34 (6H, m), 7.73-7.83 (2H, m), 8.19-8.36 (3H, m), 8.45-8.52 (1H, m), 13.95 (1H, m)

Example 57

5-(3-aminophenyl)-3-benzyl-1H-pyrazolo[4,3-c][1, 8]-naphthyridin-4 (5H)-one

To a solution of 3-benzyl-5-(3-nitrophenyl)-1H-pyrazolo [4,3-c][1,8]naphthyridin-4 (5H)-one (98 mg, 0.25 mmol) in conc. hydrochloric acid (7 ml) was added tin chloride.2H$_2$O (500 mg, 5-fold weights), and the mixture was stirred at room temperature for 1.5 hour, admixed with water, then treated with sodium carbonate to make it to pH8-9, and extracted with chloroform 8 times. The organic layer was dried over anhydrous magnesium sulfate, and evaporated to give 5-(3-aminophenyl)-3-benzyl-1H-pyrazolo[4,3-c][1,8]naphthyridin-4 (5H)-one (63 mg, 70%).

mp 277-279° C. $^1$H NMR(DMSO-$d_6$) δ:4.34 (2H, s), 5.16 (2H, s), 6.32-6.37 (2H, m), 6.59-6.61 (1H, m), 7.08-7.34 (7H, m), 8.36-8.38 (1H, app-dd, J=2.0 Hz, 4.9 Hz), 8.44-8.48 (1H, app-dd, 2.0 Hz, 7.9 Hz), 14.09 (1H, brs)

Example 58

3-benzyl-5-(3-fluorophenyl)-1H-pyrazolo[4,3-c][1, 8]-naphthyridin-4 (5H)-one

To a suspension of 1-(3-fluorophenyl)-4-hydroxy-1,8-naphthyridin-2 (1H)-one (512 mg, 2.0 mmol, obtained in Synthetic Example 31 (3)) in DMF (8 ml) was added sodium hydride (about 60%, 192 mg, 4.8 mmol, 2.4 eq.), the mixture was stirred until the production of hydrogen was completed. Next, after phenylacetyl chloride (371 mg, 2.4 mmol, 1.2 eq.) was added, the mixture was stirred at room temperature, and treated with water. The resultant DMF layer was washed with hexane, acidified with hydrochloric acid, and filtered to give precipitates which were washed with water, and then suspended in DMF (8 mL). To the suspension was added hydrazine monohydrate (80%, 224 μl, 5.6 mmol, 2.8 eq.), and the mixture was stirred overnight at 100 to 110° C. The reaction mixture was admixed with water, and filtered to give precipitates which were washed with water, then dissolved in DMF, and treated with methanol and water. The mixture was filtered to give precipitates which were washed with water and dried to afford 3-benzyl-5-(3-fluorophenyl)-1H-pyrazolo[4,3-c][1, 8]naphthyridin-4 (5H)-one (330 mg, 45%).

mp 298-299° C./DMF-MeOH—H$_2$O $^1$H NMR(DMSO-$d_6$) δ:4.35 (2H, s), 7.13-7.36 (9H, m), 7.50-7.59 (1H, m), 8.35-8.38 (1H, app-dd, J=2.0 Hz, 4.9 Hz), 8.48-8.51 (1H, app-dd, J=2.0 Hz, 7.9 Hz), 14.14 (1H, brs)

Formulation Examples

Formulation Example 1

A formula for one tablet (total amount per tablet: 150 mg) is given below:

| | |
|---|---|
| Compound of the present invention | 30 mg |
| Crystalline Cellulose | 90 mg |
| Corn Starch | 28 mg |
| Magnesium Stearate | 2 mg |

The ingredients were formulated into tablets by known methods according to general pharmaceutical rules prescribed in JPXIV.

Formulation Example 2

A formula for one capsule (total amount per capsule: 180 mg) is given below:

| | |
|---|---|
| Compound of the present invention | 50 mg |
| Lactose | 100 mg |
| Corn Starch | 28 mg |
| Magnesium Stearate | 2 mg |

The ingredients were formulated into capsules by known methods according to general pharmaceutical rules prescribed in JPXIV.

Formulation Example 3

The compound of the present invention (10 mg) was dissolved in 3 ml of physiological saline. The solution was adjusted to pH 7 with 0.1 N aqueous sodium hydroxide, to which was added physiological saline to make the total volume 5 ml. The resulting solution was dispensed to each ampule, and then subjected to heat sterilization to obtain injections.

Formulation Example 4

To a mixture of the compound of the present invention (1 g), egg yolk lecithin (1.2 g), α-tocopherol (20 mg) and ascorbic acid (33 mg) was added purified water to make the total volume 100 ml. The resulting product was used as a pharmaceutical preparation for aerosols.

INDUSTRIAL APPLICABILITY

The present invention relates to PDE IV inhibitors. The compounds of the present invention possess potent inhibiting properties toward PDE IV. The compounds inhibit PDE IV predominantly present in bronchial smooth muscle cells and inflammatory cells, thereby leading to an elevation of cAMP levels in such cells, with the result that it may be expected to achieve relaxation of bronchial smooth muscle and suppression of inflammatory cell activation. Since it is noted that the compounds have a great difference between their pharmacologically-effective dose level and their inhibitory dose level for drug-metabolizing enzymes, as compared with the prior art PDE IV inhibitors. The present invention enables the production of safer anti-asthmatics, prophylactic and/or therapeutic drugs for COPD, and others, which possess excellent pharmacological properties.

While specific details of the present invention have been described in terms of preferred embodiments and examples, it will be apparent to those of skill in the art that variations may be applied to those disclosed in the foregoing. In light of the disclosure, various modifications and rearrangements which can be made to those set forth herein are deemed to be within the spirit and scope of the appended claims.

What is claimed is:

1. A compound of the formula (1):

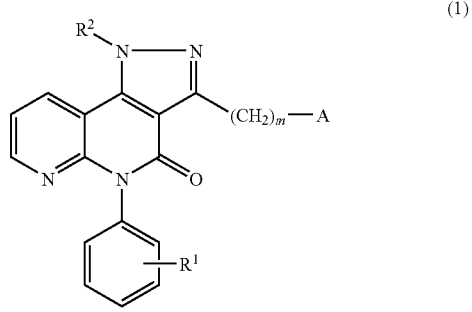

wherein:
A is phenyl, which may be unsubstituted or optionally substituted with fluorine;
$R^1$ is hydrogen;
$R^2$ is hydrogen; and
m is 1;
wherein said compound is selected from the group consisting of 3-benzyl-5-phenyl-1H-pyrazolo[4,3-c][1,8]-naphthyridin-4(5H)-one, and 3-(4-fluorobenzyl)-5-phenyl-1H-pyrazolo[4,3-c][1,8]-naphthyridin-4(5H)-one, or a pharmaceutical acceptable salt thereof.

2. A pharmaceutical composition which comprises an effective amount of a compound according to claim 1, or a pharmaceutically acceptable salt thereof, in admixture with a pharmaceutically acceptable carrier.

* * * * *